United States Patent [19]
Tanaka et al.

[11] Patent Number: 6,022,512
[45] Date of Patent: *Feb. 8, 2000

[54] METHOD OF CLEANING AND DISINFECTING HEMODIALYSIS EQUIPMENT, CLEANING DISINFECTANT, AND CLEANING AND DISINFECTING APPARATUS

[75] Inventors: Noriaki Tanaka, 707, Kitanoda, Sakai-shi, Osaka-fu; Tomiya Abe, Wakayma, both of Japan

[73] Assignee: Noriaki Tanaka, Osaka-fu, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/553,036

[22] Filed: Nov. 3, 1995

[30] Foreign Application Priority Data

| Apr. 14, 1995 | [JP] | Japan | 7-088949 |
| Jul. 4, 1995 | [JP] | Japan | 7-168500 |
| Aug. 25, 1995 | [JP] | Japan | 7-217812 |

[51] Int. Cl.[7] ............... A61L 2/18; A61M 1/14
[52] U.S. Cl. ............... 422/292; 422/1; 422/28; 134/166 C; 134/171; 210/321.69; 210/636
[58] Field of Search ............ 422/28, 292, 105, 422/116, 117, 2, 1; 210/636, 646, 321.69; 134/166 C, 169 C, 171; 204/229, 228, 263

[56] References Cited

U.S. PATENT DOCUMENTS

| 3,871,913 | 3/1975 | Shaldon | 134/22.18 |
| 3,920,030 | 11/1975 | Mason | 134/58 R |
| 4,166,031 | 8/1979 | Hardy | 134/22.17 |
| 4,789,467 | 12/1988 | Lindsay et al. | 422/116 |
| 5,279,799 | 1/1994 | Moser | 422/292 |
| 5,304,349 | 4/1994 | Polaschegg | 422/105 |
| 5,445,722 | 8/1995 | Yamaguti et al. | 204/229 |
| 5,447,686 | 9/1995 | Seidner | 422/1 |

FOREIGN PATENT DOCUMENTS

| 0612694 | 8/1994 | European Pat. Off. . |
| 0722740 | 7/1996 | European Pat. Off. . |
| 7-108064 | 4/1995 | Japan . |
| 7116247 | 5/1995 | Japan . |
| 07284744 | 10/1995 | Japan . |
| 7-284744 | 10/1995 | Japan . |
| 8-252310 | 10/1996 | Japan . |
| WO 9309821 | 5/1993 | WIPO . |

OTHER PUBLICATIONS

Derwent Publications Ltd., London, GB, Database WPI, SU 1752401, Aug. 7, 1992.

*Primary Examiner*—Hien Tran
*Attorney, Agent, or Firm*—Sughrue, Mion, Zinn, Macpeak & Seas, PLLC

[57] ABSTRACT

Disclosed are a cleaning and disinfecting method for treating the surfaces of hemodialysis equipment which are exposed to a dialysate or pure water which comprises the use of electrolyzed hyperacidity water for cleaning and disinfection, as well as a cleaning disinfectant consisting of electrolyzed hyperacidity water, and a cleaning and disinfecting apparatus. The method insures effective cleaning and disinfection and even elimination or inactivation of endotoxins in a reduced time, efficiently, and with reduced water consumption.

14 Claims, 12 Drawing Sheets

F I G. 4
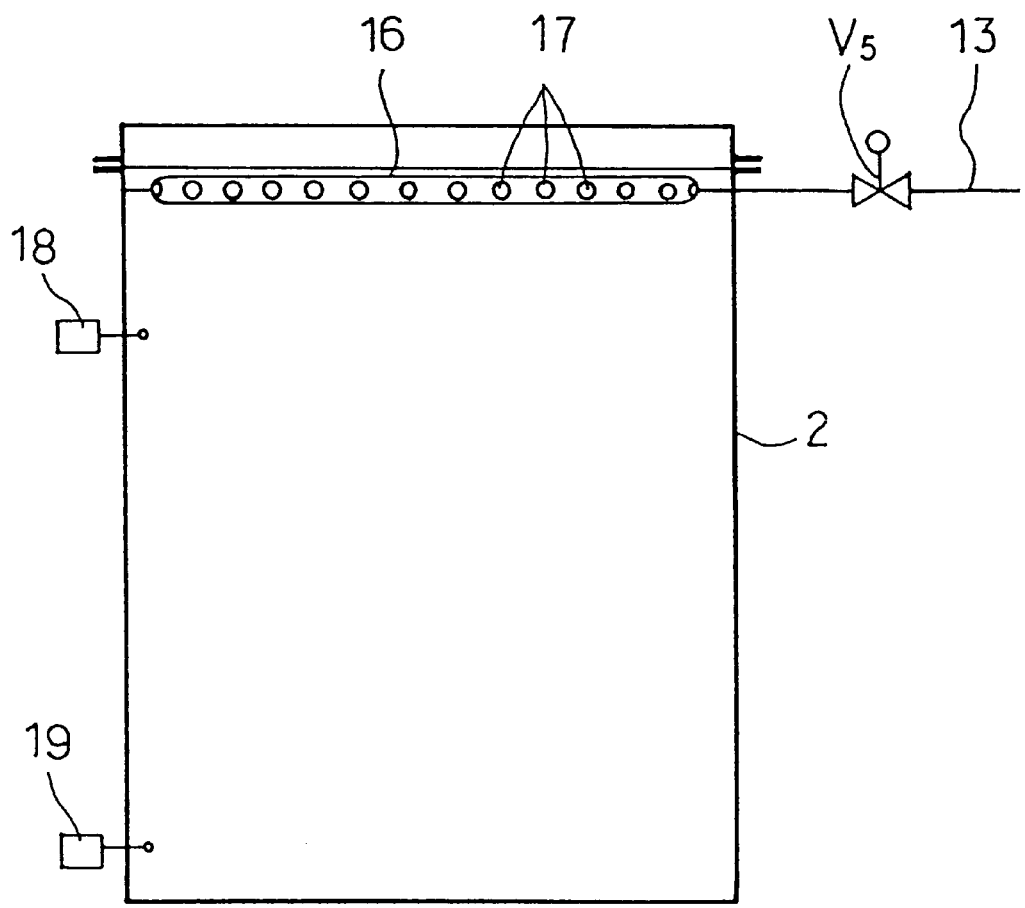

METHOD OF CLEANING AND DISINFECTING HEMODIALYSIS EQUIPMENT, CLEANING DISINFECTANT, AND CLEANING AND DISINFECTING APPARATUS

FIELD OF THE INVENTION

This invention relates to a method of cleaning and disinfecting hemodialysis equipment, a cleaning disinfectant or cleaning agent, and a cleaning and disinfecting apparatus.

BACKGROUND OF THE INVENTION

Hemodialysis is conventionally instituted in patients with, for example, renal failure. When one suffers from renal failure, various toxins which are normally excreted in the urine are accumulated in the body and the excess water retained due to a decrease in urine volume leads to unbalance of electrolytes in the body fluid so that various signs of acidosis tend to appear. Therefore, a hemodialysis equipment provided with an artificial kidney (dialyzer) is employed to briny the blood into contact with a dialysate through the semipermeable membrane of the dialyzer to remove the uremic toxin and excess water and thereby normalize the electrolytes and improve signs of acidosis.

The hemodialysis equipment used for this purpose varies in scale ranging from a personal or individual equipment designed for hemodialysis of a single individual to a multiple-patient hemodialysis equipment for the concurrent hemodialysis of tens of patients Generally, however, any hemodialysis equipment is a system comprising the following principal components.

(1) a patient monitor (also termed "bedside console"), to which an artificial kidney (dialyzer) comprising A hollow fiber semipermeable membrane is connected;

(2) a dialysate supply unit (also termed "central") which dilutes dialysate A and dialysate B stock solutions with purified water to prepare a dialysate and feeds the prepared dialysate to said patient monitor;

(3) a pipeline system interconnecting said patient monitor and dialysate supply unit;

(4) a water treatment unit comprising a cartridge filter, an activated carbon filter, a soft water-making device, a reverse osmosis unit (RO unit) and the like which prepares a pure diluont water from tap water for the preparation of said dialysate; and (5) a tank for each of said dialysate A stock solution and dialysate B stock solution for the preparation of said dialysale.

Said dialysate A stock solution generally comprises calcium ion and magnesium ion sources, and typically comprises sodium chloride, potassium chloride, calcium chloride, magnesium chloride, sodium acetate, glucose and the like in a high concentration. Said dialysate B stock solution is generally an aqueous solution of sodium bicarbonate.

Among the above components of hemodialysis equipment, particularly the dialysate B stock solution tank is opened and closed for introduction of the solvent for dialysate B and preparation of dialysate B stock solution, and should hold the solution throughout the hemodialysis session of the day. Moreover, the concentration of, for example, sodium bicarbonate is low. For these reasons, the system is liable to pick up falling bacteria and other microorganisms, with the result that the pipeline within said dialysate supply unit, the dialysate supply line system, and the dialysate line in said patient monitor, among others, are liable to become contaminated with bacteria and endotoxins.

The dialysate supply unit, dialysate supply line system, and the internal dialysate line of the patient monitor are used repeatedly for a long time and the regions of stagnant flow and precipitated carbonate (calcium carbonate) deposits within the lines serve as favorite habitats for bacteria and production of endotoxins, and the contaminated lines favor a further proliferation of bacteria. Moreover, the intra-pipeline fouling with the low molecular weight proteins removed by a high performance membrane dialyzer has recently been pointed out.

Meanwhile, the pure water (generally known as "RO processed water") prepared using an RO membrane such as one used in reverse osmosis apparatus is stored in a hermetically closed RO processed water tank where it is warmed, degassed, used for diluting dialysate stock solutions, for rinse before and after each hemodialysis session, and for dilution of a cleaning disinfectant (cleaning agent), but since it is chlorine-free water, bacteria and endotoxins tend to multiply owing to convection of RO processed water and injury of the RO membrane.

Moreover, since dialysate A stock solution is a high concentration solution containing a small amount of acid, it was formerly believed to be free of bacteria and endotoxins. Actually, however, because the tank is frequently opened and closed, the possibility of contamination has recently been pointed out.

The endotoxins mentioned above exist in the outer cell wall layer of gram-negative bacteria, particularly gram-negative bacilli, and is a lipopolysaccharide (LPS) composed of hydrophilic polysaccharides and hydrophobic lipid A. The endotoxin has activity to induce a variety of humoral factors such as interleukin-1 (IL-1), tumor necrosis factor (TNF) and interferons (IFN), pyrogenicity, fatal toxicity, and activity to cause tissue necrosis, and is omnipresent, for example in tap water, atmospheric air, etc. and on hands and articles.

Dialysis patients show a high positive rate for anti-endotoxin antibodies. Moreover, since the production of IL-1 is more liable in dialysis patients, it is essential to insure that the dialysate and dialysato lines (dialysate circuit) be endotoxin-free.

Furthermore, with the recent use of high performance membranes or highly permeable membranes in clinical practice, back filtration or back diffusion during hemodialysis tends to introduce pyrogens into the patient's blood to cause fever and other adverse reactions in the patient, thus presenting a major clinical problem. It is considered that endotoxins are the most active and most frequent of all pyrogens.

Since multiplication of bacteria and production of large amounts of endotoxins exert adverse effects on the patient, it is a conventional practice to clean and disinfect the dialysis equipment or dialysis machine with a chemical agent such as sodium hypochlorite, acetic acid and/or formalin after the daily dialysis session.

Moreover, with the recent popularity of bicarbonate-containing dialysates, precipitation of the carbonate (calcium carbonate) in the dialysate circuit tends to cause a trouble in the patient monitor, and in order to remove such carbonate deposits, the circuit is generally washed with an acid such as glacial acetic acid, hydrochloric acid or citric acid.

These conventional cleaning disinfectants are more or less satisfactory for disinfection purposes, but because they are highly toxic, these substances must be thoroughly rinsed off with water after use. This rinse procedure requires a large volume of water.

Furthermore, certain conventional cleaning and disinfecting agents such as sodium hypochlorite and formalin have irritating odors and interfere with the cleaning operation, and may cause a stinging pain or ill effects on the mucosa.

Furthermore, the conventional routine cleaning and disinfecting procedure is not sufficiently effective to remove or inactivate endotoxins, and the endotoxin concentration undergoes a progressive increase as the dialysate flows through the dialysis system so that it is frequently found that there is substantially no disparity between the endotoxin concentration in the patient monitor and the endotoxin concentration in tap water.

To avoid such adverse effecLs or endotoxins, a reverse osmosis membrane (RO membrane) is generally used in the water treatment unit for removing endotoxins from tap water. Although endotoxins in tap water can be eliminated by such a water treatment unit, the disinfectant chlorine contained in tap water is also eliminated at the same time so that even when the water purified by an RO membrane (RO processed water) is used for the preparation of a dialysate, the dialysate is sometimes subject to the influence of bacteria.

Meanwhile, filters for removing endotoxins have also been developed and proved to be effective to a certain degree but the installation of such an endotoxin filter introduces other problems such as increased initial cost, complication of the dialysis system, and aging of the filter through adsorption of endotoxins.

SUMMARY OF THE INVENTION

There is, therefore, a demand for development of a cleaning and disinfecting method and agent, particularly for the elimination or inactivation of endotoxins, which are superior in effect, efficiency and cost.

An object of this invention, therefore, is to provide a cleaning and disinfecting method by which the points of a dialysis equipment to be cleaned, typically the internal tubing of the dialysate supply unit which is exposed to the dialysate, the internal dialysate line of the patient monitor, the lines interconnecting the component units, the RO processed water tank or the water treatment unit, the dialysate A stock solution tank, and the dialysate B stock solution tank, can be effectively disinfected (sterilized), with simultaneous removal or inactivation of endotoxins, with improved efficiency, improved Lime economics, and reduced water consumption.

Another object of this invention is to provide a cleaning disinfectant or cleaning agent suitable for use in reducing the above method to practice.

As the result of intensive research for accomplishing the above object, the inventor of this invention paid attention to the possibility of using electrolyzed hyperacidity water (or hyperacidity electrolyzed water) for the cleaning disinfectant or cleaning agent.

However, the use of electrolyzed hyperacidity water for such purposes had not been attempted to date, nor had the effecl of its use on the dialysis patient been known. Moreover, all the information available on electrolyzed hyperacidity water was its bactericidal activity, and it was not known at all that such water was ever possessed of the activity to inactivate or remove endotoxins. Furthermore, since electrolyzed hyperacidity water as such is unstable and reportedly loses its bactericidal activity in the presence of organic matter such as protein, there was the apprehension that its bactericidal activity might be lost in the process of its flowing through the dialysate circuit of the hemodialysis delivery system or hemodialysis equipment.

Surprisingly, however, the inventor discovered that electrolyzed hyperacidity water, when used as a cleaning disinfectant, not only provides bactericidal effects but also insures effective elimination or inactivation of endotoxins, which could not be adequately accomplished by the conventional cleaning technology, and further found that additionally these effects are sustained even to the terminal end of the dialysate line being cleaned, and that it exerts no ill effect on the patient and the dialysis equipment. We continued further research, and accomplished the present invention.

This invention, therefore, provides a method of cleaning and disinfecting the surfaces of homodialysis equipment which are exposed to dialysate or pure water with a cleaning disinfectant characterized in that electrolyzed hyperacidity water is used as said cleaning disinfectant.

More particularly, this invention provides a method of eliminating or inactivating endotoxins which comprises bringing electrolyzed hyperacidity water into contact with the surfaces of hemodialysis equipment which are exposed to the dialysate or pure water.

The invention further provides a cleaning disinfectant or cleaning agent for hemodialysis equipment characterized in that it consists of electrolyzed hyperacidity water.

BRIEF DESCRIPTION OF THE DRAWINGS

FIG. 4 is a longitudinal section view showing a mode of cleaning and disinfecting a dialysate B stock solution tank in accordance with this invention;

DETAILED DESCRIPTION OF THE INVENTION

Figure 1:
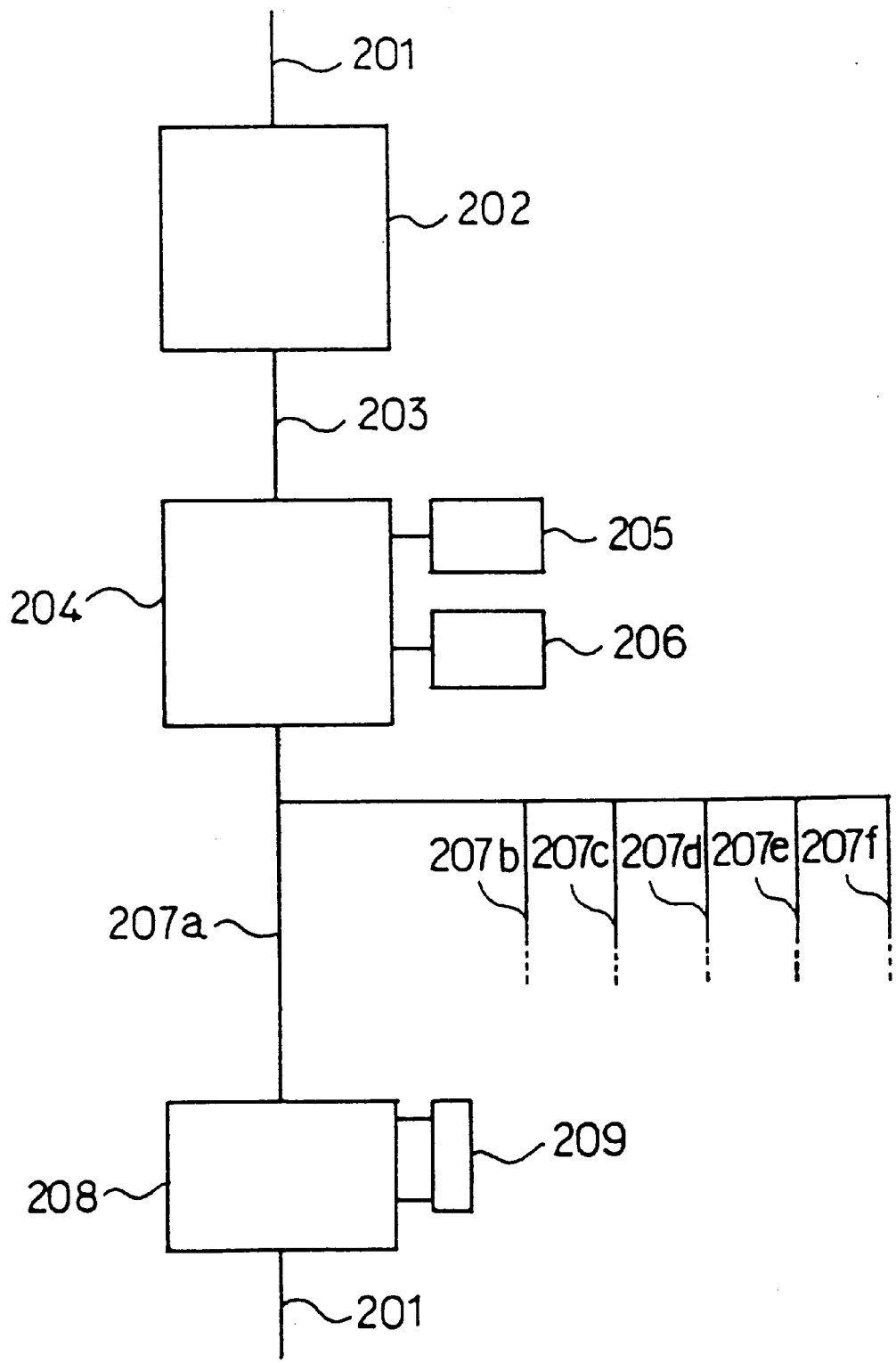
FIG. 1 is a simplified schematic diagram illustrating a multiple patient dialysis equipment or dialysis system.

This invention is now described in detail.

A typical mode of operation of a hemodialysis equipment to be cleaned and disinfected by the cleaning and disinfecting method of this invention is first described with reference to FIG. 1 which is a simplified illustration of a multiple-patient dialysis system.

Tap water from a line 201 is treated in a water treatment unit 202, where electrolytes such as calcium, magnesium, etc., residual chlorine, and suspended matter are removed to provide pure water. Generally, this pure water is preferably the RO processed water prepared by using a reverse osmosis membrane (RO membrane) in the water treatment unit 202.

The pure water thus prepared is transported via a line 203 into a multiple-patient dialysate supply unit 204, where a dialysate A stock solution and a dialysate B stock solution from a dialysate A stock solution tank 205 and a dialysate B stock solution tank 206, respectively, are diluted and blended in a predetermined ratio in a mixing tank to provide a dialysate. This dialysate is normally stored in a dialysate storage tank within the dialysate supply unit 204.

The dialysate prepared in the above manner is fed to patient monitor 208 via a distribution line 207a. FIG. 1 shows only a dialyeate supply unit 204, a distribution line 207a, and a patient monitor 208, but since tho system is actually a multiple-patient dialysis system, it includes a plurality of branch lines 207b, 207c, 207d, 207e, 207f, etc., all branching out from the distribution line 207a, and a plurality of patient monitors (not shown) connected to said branch lines. The dialysis system to which this invention is applicable may be a still larger system comprising a plurality of dialysate supply units each connected to a plurality of distribution lines and a plurality of patient monitors.

The patient munilor 208, also known as a console, provides for safe supply of a dialysate from a multiple-patient dialysate supply unit 204 and uneventful extracorporeal circulation of the patient's blood. The patient monitor is generally divided into the dialysate circuit (dialysate side) and the blood circuit (blood side). The dialysate circuit comprises a dialysate temperature controller, a dialysate pressure gauge, a thermometer, a dialysate flowmeter, a blood leak detector, and a UF (ultrafiltration)-controller, among other components, while the blood circuit includes a blood pump, an arterial negative pressure monitor, an arteriovenous pressure monitor, an air detector, and an anticoagulant infusion device, among other components. These components function in association to monitor the real-time status of dialysis throughout the whole dialysis session and control the system to meet the parameter settings.

The patient monitor 208 is connected to an artificial kidney or dialyzer 209. In the dialyzer 209, the blood in extracorporeal circulation are brought into contact with the dialysate through a semipermeable membrane to remove the uremic toxin and water, whereby the electrolyte concentrations are adjusted and acidosis is corrected.

The dialysate which has undergone an exchange of substances with the blood in the dialyzer 209 is discharged as an effluent from a line 210.

Figure 2:
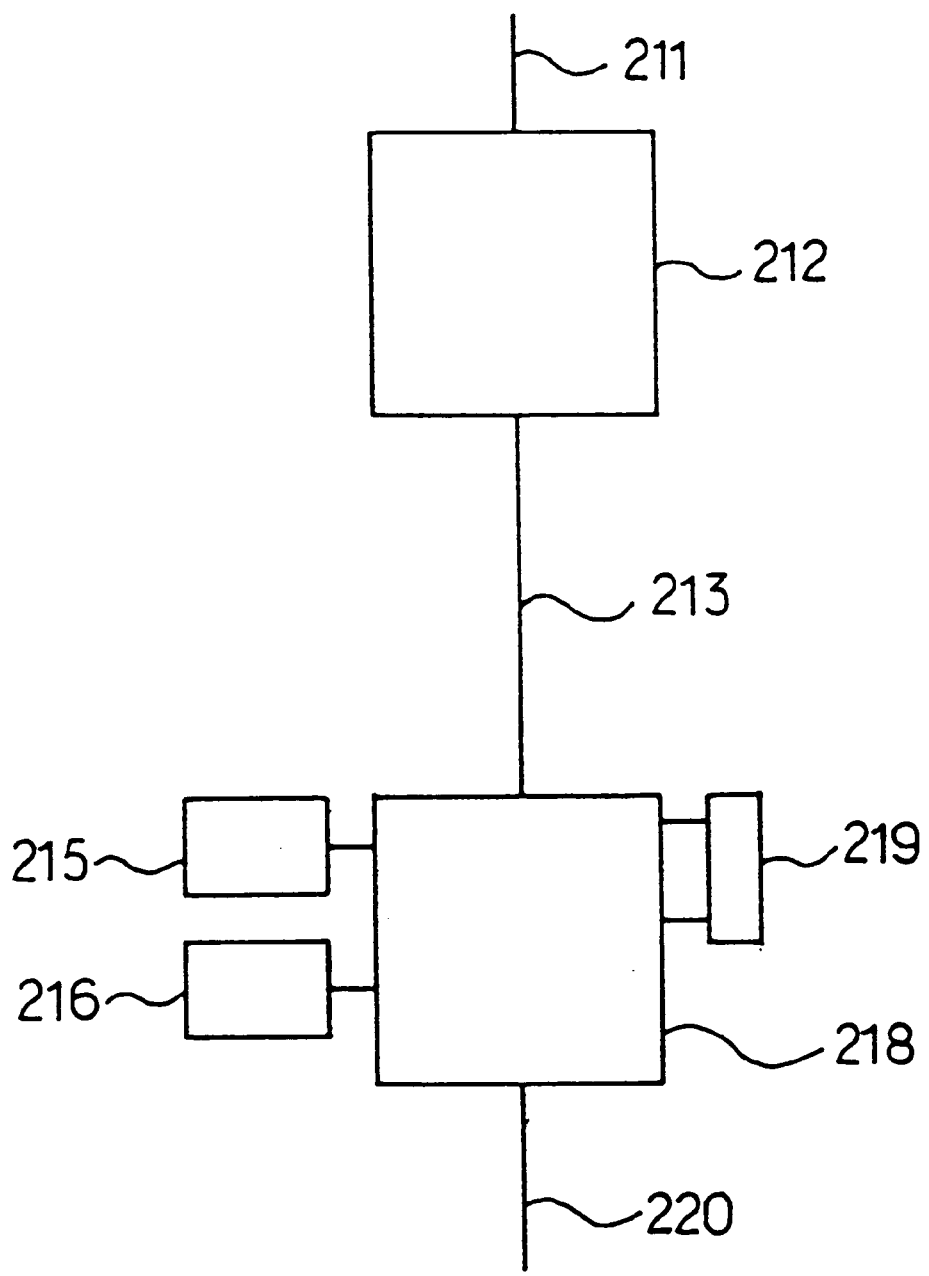
FIG. 2 is a schematic diagram illustrating a personal or individual dialysis equipment or dialysis system.

A simplified illustration of the personal or individual dialysis system is shown in FIG. 2. As in the system shown in FIG. 1, tap water from a line 211 is introduced into a water treatment unit 212 where it is treated for the preparation of pure water. The resulting pure water flows through a line 213 to a personal dialysis equipment 218 comprising an integral assembly of a dialysate supply means and a patient monitor means, where a dialysate A stock solution and a dialysate 13 stock solution from a dialysate A stock solution tank 215 and a dialysate B stock solution tank 216 are diluted and blended in a predetermined ratio to prepare a dialysate. The resulting dialysate is fed to a dialyzer 219 where, under the control of the built-in patient monitor of the dialysis machine 218, the dialysate undergoes an exchange of substances with the blood in extracorporeal circulation and is discharged as an effluent from a line 220.

Concerning the mechanism and fundamental structure, the personal dialysis equipment is basically identical with the multiple-patient dialysis equipment described hereinbefore except that the dialysate supply means and the patient monitor means are integrally assembled and, are accommodated, generally together with the dialysate A stock solution tank 215 and the dialysate B stock solution tank 216, in one compact console.

The cleaning and disinfecting method of this invention cleans and disinfects the points or surfaces which are likely to be contaminated with bacteria and endotoxins within the dialysis equipment or dialysis machine, particularly the surfaces exposed to the dialysate or pure water.

Specifically, the points to be cleaned and disinfected by the method of this invention are (1) the accessory lines and tanks of the dialysate supply unit, e.g. the dialysate mixing tank, dialysate storage tank and dialysate line within the dialysate supply unit, the line connecting the dialysate supply unit with the patient monitor, and the dialysate line within the patient monitor, (2) the accessory lines and tanks of the water treatment unit, e.g. the pure water tank and the line connecting said tank with the dialysate supply unit, and (3) the dialysate A stock solution tank and dialysate B stock solution tank.

The points to be cleaned and disinfected within the dialysate circuit are the lines and tanks (supply tank etc.) which are exposed to pure water, dialysaLe stock solution and prepared dialysate within the dialysate supply unit and the inside wall of the dialysate line within the patient monitor and the inside wall of the line connecting these components with each other The dialyzer 209 is a sterilized disposable module which is used only during hemodialysis and then discarded. Therefore, the feed and discharge means on the dialysate circuit are disconnected from the dialyzer and coupled for cleaning and disinfection. In the context of this invention, this coupled line system is included in the internal dialysate circuit of the patient monitor which is to be cleaned and disinfected.

If necessary, the water treatment unit, particularly the inside wall of its pure water tank, is also cleaned and disinfected.

Furthermore, the dialysate A stock solution tank and the dialysaLe B stock solution tank may also be cleaned and disinfected.

With regard to these tanks, since the dialysate A stock solution is a highly concentrated solution containing sodium chloride, potassium chloride, glucose and the like and contains a small amount of acid, it seldom happens that bacteria grow in these tanks. However, since the dialysate B stock solution is a solution of low concentration containing sodium bicarbonate etc. and, as such, is little bacteriostatic, thus allowing growth of bacteria, the dialysate B stock solution tank is preferably cleaned and disinfected.

Referring to FIG. 1, the points to be cleaned and disinfected with particular emphasis in the multiple-patient dialysis system or dialysis equipment are the line 203, the internal lines and storage tanks of the dialysate supply unit 204, the dialysate B stock solution tank 206, the lines 207a–207f interconnecting the dialysate supply unit 204 and patient monitors 208, and the internal dialysate lines within the patient monitors 208.

Referring to FIG. 2, the points to be cleaned and disinfected with particular emphasis in the personal dialysis equipment are the line 213, the internal dialysate line of the console 218, and the dialysate B stock solution tank 216.

The electrolyzed hyperacidity water for usc as the cleaning disinfectant in this invention is produced by electrolysis of water containing a small amount or trace amount of sodium chloride with use of a diaphragm, and has a pH value of not more than 2.7 and a redox potential (or oxidation-reduction potential) of at least 1000 mV. Such water is conventionally known, and also called hyperacidity electrolyzed water'.

Today various models of electrolyzed hyperacidity water generators are commercially available from a number of manufactures, and the method of this invention can be carried out using the electrolyzed hyperacidity water produced by any of such commercially available electrolyzed hyperacidity water generators.

In this invention, it is preferable to use such electrolyzed hyperacidity water having a pH value of about 2.7–2.3, particularly about 2.7–2.4, and a redox potential of about 1000–1200 mv, particularly about 1100–1150 mV. In addition, it is preferable that the electrolyzed hyperacidity water for use in this invention has an effective chlorine concentration of about 10–40 ppm, particularly about 15–30 ppm.

The cleaning method of this invention is generally practiced in the following manner.

After a hemodialysis session, the cleaning and disinfectant or cleaning agent of this invention, namely one consisting of said electrolyzed hyperacidity water, is introduced into the above-mentioned dialysate circuit in the first place so that it may contact the surfaces to be cleaned in the dialysate circuit.

After the hemodialysis session and before the cleaning and disinfection with electrolyzed hyperacidity water, the dialysate circuit is preferably post-rinsed with water. The preferred water for use in this post-rinse procedure is generally a bacteria-free and endotoxin-free RO processed water prepared in the water treatment unit.

Conventionally, this post-rinse is carried out over a long time for driving out the residual dialysate and the organic matter that might detract from disinfection effect from the circuit and for washing out the bacteria and endotoxins. With the cleaning disinfectant of this invention, namely said electrolyzed hyperacidity water, presumably because of its high bactericidal activity and high activity to eliminate or inactivate endotoxins, the quantity of water required for the post-rinse or the post-rinse time is reduced to about ¼–⅔, particularly about ¼–½, as compared with the conventional cleaning disinfectants.

Taking a multiple-patient dialysis equipment tor 30 patients as an example, and assuming that the flow rate per patient monitor is about 400–600 ml/minute, particularly about 500 ml/minute, it has been found that whereas the conventional post-rinso time is generally about 60 minutes, though it varies somewhat with hemodialysis hospitals or hemodialysis facilities, the post-rinse time according to this invention is generally as short as about 15–30 minutes.

In the method of this invention, all all is necessary is to insure that electrolyzed hyperacidity water be brought into contact with the surfaces to be cleaned and disinfected, such as the surfaces exposed to the dialysate in the dialysate circuit, the inside wall of the pure water tank, and the inside walls of the dialysate A and B stock solution tanks, for instance. The method for insuring such contact is not limited.

As to the surfaces to be cleaned and disinfected within the dialysate circuit, it is basically sufficient to load or fill up the dialysate circuit with said electrolyzed hyperacidity water so that the entire internal surface of the system may be exposed to said electrolyzed hyperacidity water.

According to the research carried out by the present inventor, there is a tendency that the bactericidal activity of electrolyzed hyperacidity water is not sustained for a long time, and therefore it is preferable to continuously feed electrolyzed hyperacidity water to the dialysate circuit so as to effect continuous flow thereof, whereby the initial pH and redox potential of the electrolyzed hyperacidity water can be successfully maintained even in the internal dialysate line of the terminal patient monitor which is remotest from the dialysate supply unit. Generally, the freshly prepared electrolyzed hyperacidity water so used for cleaning and disinfection is preferably discarded as an effluent.

The continuous feeding of electrolyzed hyperacidity water through the dialysate line system can be achieved by various routine techniques, and there is no particular methodological limitation. Generally, electrolyzed hyperacidity water is preferably introduced from the line (e.g. line 203 in FIG. 1) interconnecting the water treatment unit and the dialysaLe supply unit or introduced first into the dialysate storage tank, and then distributed, via the downstream lines (distribution lines connecting the dialysate supply unit to the patient monitors), to the patient monitors to clean and disinfect them all at once and, thereafter, discharged from the effluent lines of the patient monitors (e.g. line 210 in FIG. 1).

The feeding conditions can be suitably selected from a broad range but generally it is advantageous, from operation points of view, to employ the conditions which are the same as, or similar to, those used for feeding the dialysate in the particular dialysis equipment to be cleaned and disinfected.

There is no particular limitation, either, on the temperature at which the cleaning and disinfection operation is carried out. Generally this operation can be carried out at a temperature of about 10–40° C., preferably at ambient temperature, but a somewhat higher or lower temperature may be employed where appropriate.

The cleaning and disinfecting time is not particularly restricted, either, so far as the cleaning and disinfecting operation is conducted until bacteria and endotoxins from the dialysate circuit is no more detected. Thus, the cleaning and disinfecting time can be selected according to the scale of the dialysis system, the feeding rate of electrolyzed hyperacidity water and the like. The cleaning disinfectant of this invention, namely said electrolyzed hyperacidity water, has high bactericidal activity and high activity to inactivate endotoxins and, compared with the conventional cleaning disinfectants, the quantity or feeding time can be reduced to about ⅐–⅔, particularly about ¼–½ of the conventional quantity or feeding time of conventional disinfectants.

Taking a multiple-patient dialysis equipment for a central treatment of about 30 patients as an example and assuming that the cleaning and disinfection procedure is carried out at ambient temperature and that the feeding rate per patient monitor is set at about 400–600 ml/minute, particularly about 500 ml/minute, the necessary cleaning and disinfecting time is about 30 minutes with the conventional disinfectants. On the other hand, it takes only about 4 minutes for the cleaning disinfectant of this invention to achieve an equivalent effect, and even if a thorough disinfection is desired, a cleaning time of, at most, about 20 minutes will suffice.

Generally, the cleaning and disinfection of the lines and tanks exposed to the dialysate is preferably carried out daily after completion of hemodialysis of the day. Thus, upon completion of the final hemodialysis session of the day, the dialysis equipment is post-rinsed, and then subjected to the above cleaning and disinfection procedure in accordance with the present invention. As an alternative, the dialysis equipment is post-rinsed with water, and the cleaning disinfectant, namely said electrolyzed hyperacidity water, is introduced into the dialysate circuit or dialysate line of the dialysis equipment, allowed to stand in said dialysate circuit overnight and is flushed out with rinse water on the following morning. Generally, the rinse water used for this purpose is preferably a bacteria-free and endotoxin-free RO processed water prepared in the water treatment unit.

The electrolyzed hyperacidity water for use as the cleaning disinfectant in this invention is low in toxicity and substantially harmless. Thus, since the above-mentioned properties of this water are lost on dilution with an adequate amount of water and therefore the water can be handled substantially in the same way as ordinary water, the electrolyzed hyperacidity water can be simply driven out after the cleaning and disinfection operation without need for any subsequent procedure. Therefore, the quantity of water required for pre-rinse (rinse before start of dialysis) of the disinfected equipment may be as small as about $1/4$–$2/3$, particularly about $1/4$–$1/2$, as compared with the conventional practice.

Taking a multiple-patient dialysis equipment for a central treatment of about 30 patients as an example and assuming that the flow rate per patient monitor is about 400–600 ml/minute, particularly about 500 ml/minute, the conventional pre-rinse time is generally about 60 minutes, though it varies somewhat with different hemodialysis hospitals or hemodialysis facilities. In the case of this invention, however, a pre-rinse time of about 15–30 minutes is generally sufficient The water treatment unit of the dialysis equipment may also be cleaned and disinfected, for example, by withdrawing pure water from its pure water tank and showering the tank with electrolyzed hyperacidity water or by forming a closed circuit and circulating electrolyzed hyperacidity water through the whole or part of the water treatment unit.

There is no particular limitation on the temperature at which this cleaning and disinfection is carried out. Generally, this operation can be carried out at about 10–40° C., preferably at ambient temperature, but a somewhat higher or lower temperature may be employed where necessary. The cleaning and disinfecting time and the quantity of electrolyzed hyperacidity water to be used are dependent on the capacity and structure of the pure water tank but when, for example, a pure water tank of about 500-liter capacity is to be cleaned by the above-mentioned showering procedure, it is generally sufficient to use about 10–20 liters of electrolyzed hyperacidity water per showering and to effect the showering for about 5 minutes.

Regarding this cleaning and disinfection of the water treatment unit, it is advisable to check, with a frequency of once in 1–3 months, for the number of bacteria and quantity of endotoxins in the pure water and perform the cleaning and disinfection when the values found are beyond certain allowable limits.

The dialysate A stock solution tank and dialysate B stock solution tank may also be cleaned and disinfected with electrolyzed hyperacidity water by the per se known technique, e.g. by sealing said electrolyzed hyperacidity water into the tanks or passing said strongly acidic water through the tanks at an appropriate flow rate. There is no particular limitation on the temperature at which this cleaning and disinfection is carried out Generally the procedure can be carried out at about 10–40° C., preferably at ambient temperature, but a somewhat higher or lower temperature may be employed where necessary. After this cleaning and disinfection, the tanks are preferably rinsed with RD processed water. The generally recommendable cleaning schedule is once a month for the dialysate A stock solution tank and once a day for the dialysate B stock solution tank.

For the rinse following the cleaning and disinfection of the water treatment unit and dialysate A and B stock solution tanks, too, the quantity of water required can be small as compared with the conventional method, and therefore the cleaning and disinfection operation can be completed in a reduced time so that the next dialysis session can be initiated as early.

In accordance with this invention, not only bacteria are destroyed or eliminated but also endotoxins, which could not be sufficiently removed or inactivated by the conventional technology, can be effectively eliminated or inactivated.

Furthermore, the bactericidal activity and endotoxin-eliminating or inactivating activity of electrolyzed hyperacidity water are well sustained even at the terminal end of the dialysate circuit being cleaned and disinfected.

While the conventional technology requires a rinse with a large quantity of water following a cleaning and disinfection procedure, the technology according to this invention requires only a small quantity of rinse water, with the result that the cleaning and disinfection operation can be completed in a short time, thus contributing to reduced cost and improved running efficiency.

The electrolyzed hyperacidity water for use in this invention does not interfere with the operation Moreover, if a portion of the electrolyzed hyperacidity water used remains in the system owing to a mechanical or other trouble, there will be no hazardous effect because the electrolyzed hyperacidity water loses most of its activities when diluted with an adequate amount of water, and can then be handled as if it were ordinary water. Thus, since highly irritating or toxic cleaning agents such as sodium hypochlorite, formalin, etc. are no longer employed, there is substantially no risk of adverse effects on the operator and the patient.

There are no such problems as corrosion of the dialysis hardware and adverse effects on the dialyzer semipermeable membrane, either.

Furthermore, whereas the conventional technology calls for acid washing with acetic acid, citric acid, hydrochloric acid or the like for removing the carbonate, the method of this invention comprising the use of electrolyzed hyperacidity water, which is acidic per se and effective in removing the carbonate, would not require acid washing or would require acid washing with a reduced frequency.

Moreover, since electrolyzed hyperacidity water is extremely low in toxicity as compared with the conventional cleaning disinfectants, the method of this invention is advantageous in that the load on the waste water treatment facility is reduced.

The foregoing method of this invention can be implemented in a variety of ways, but it is especially advantageous to carry out the method using a cleaning and disinfecting apparatus for hemodialysis equipment such as the one described hereinafter.

Figure 12:
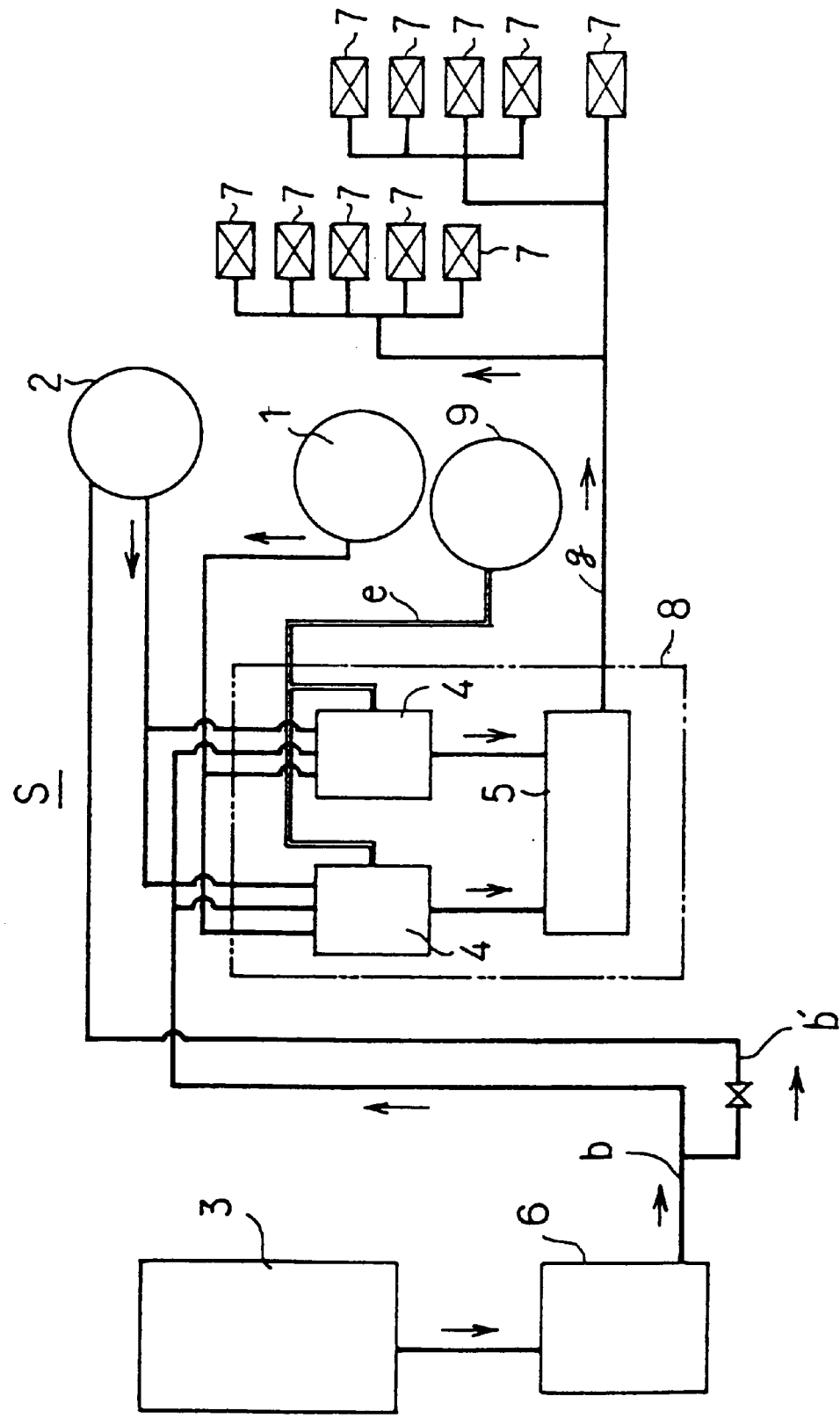
FIG. 12 is a schematic diagram showing the conventional cleaning and disinfecting apparatus.

The hemodialysis equipment or system (hereinafter referred to sometimes as 'dialysis system') has a construction as summarized in FIG. 12. Referring to FIG. 12, the dialysis system is generally represented by the symbol S. In FIG. 12, a dialysate A stock solution tank is indicated at 1, and a dialysate B stock solution tank is designated 2. The water treatment unit, which is designated 3, comprises, for example, a cartridge filter, activated carbon filter, soft water plant, reverse osmosis unit (RO unit) or the like, and makes, from tap water, diluent pure water to provide a dialysate. A tank 4 is adapted to blend the dialysate A stock solution from the tank 1 with the dialysate B stock solution from the tank 2 using the pure water (RO processed water) from the water treatment unit 3 to dilute the dialysate stock solutions. A tank 5 is adapted to store the dialysate from the tank 4. A tank 6 is adapted to store the pure water (RO processed water) from the water treatment unit 3. A patient monitor (bedside console) 7 is connected to a hemodialyzer (dialyzer). A line g connecting the tank 5 to the patient monitor 7 serves as a dialysate supply line (upstream side of the dialyzer) in the dialysate circuit. The above tanks 4 and 5 are combinedly known as the dialysate supply unit (central). The numeral 8 in FIG. 12 represents the dialysate supply unit (central). In FIG. 12, the dialyzer, the line connecting the patient monitor 7 to the dialyzer, and the blood circuit are not shown.

As the means for sterilizing and disinfecting a dialysis system, the device illustrated in FIG. 12 and the one disclosed in Japanese Unexamined Patent Publication (Kokai) No. 116247/1995 are already known.

In the device illustrated in FIG. 12, a cleaning disinfectant tank 9 is disposed alongside dialysis system S and the cleaning disinfectant such as sodium hypochlorite solution, acetic acid or formalin in the disinfectant tank 9 is supplied via line e to the tank 4 in dialysate supply unit (central) B. By this scheme, only the tank 4 and downstream components can be is disinfected. Moreover, these cleaning disinfectants are highly toxic and, therefore, have the disadvantage that after the disinfection operation they must be removed by thorough rinse. In addition, for the elimination or inactivation of endotoxins, pure water (RO processed water) for post-rinse is fed from tank 6 to tank 4 via line b and to tank 2 via b' after a hemodialysis session and prior to cleaning and disinfection. Even then, the effect is not sufficient.

In the cleaning and disinfection system described in Japanese Unexamined Patent Publication (Kokai) No. 116247/1995, the alkaline water and acidic water obtained by electrolysis of an aqueous solution of sodium chloride are used for the cleaning and disinfection of the pipelines of a dialysis system For this purpose, the pipeline on the dialysate supply side, the pipeline on the dialysate discharge side, the pipeline on the return blood side, and the pipeline on the blood withdrawal side are disconnected from the dialyzer. Then, these pipelines are coupled by means of couplers to make an open circuit, and cleaned and disinfected by passing said alkaline water and said acidic water in that order from one end of the circuit. This prior art technology is never efficient, since the pipelines must be reassembled into the open circuit for cleaning and disinfection. Moreover, this cleaning and disinfection method is not amenable to automation.

It is an object of this invention on the cleaning and disinfecting apparatus to provide a cleaning and disinfecting apparatus for dialysis system which is capable of cleaning and disinfecting endotoxins and bacteria in the tank for diluting and blending dialysate A and B stock solutions in the dialysate supply unit (central), or endotoxins and bacteria upstream as well as downstream or the portion corresponding to the tank, and also capable of cleaning and disinfecting endotoxins and bacteria without or substantially without modifying the existing dialysis system.

It is a further object of the invention to provide a cleaning and disinfecting apparatus for a dialysis system which can be efficiently applied to the cleaning and disinfection of endotoxins and bacteria and adapted to automatic cleaning and disinfection.

(1) This invention provides a cleaning and disinfecting apparatus for hemodialysis equipment or hemodialysis system characterized in that it comprises a tank for holding electrolyzed hyperacidity water and a line for transporting said electrolyzed hyperacidity water from said tank to a dialysate B stock solution tank.

(2) The above cleaning disinfecting apparatus (1) may further comprise a line for transporting electrolyzed hyperacidity water which extends from said tank for holding electrolyzed hyperacidity water to a tank for blending dialysate A and B stock solutions and diluting the mixture with pure water.

(3) Alternatively, the above cleaning disinfecting apparatus (1) may further comprise a line for transporting electrolyzed hyperacidity water which extends from said electrolyzed hyperacidity water tank to a tank for holding pure water.

(4) This invention further provides a cleaning and disinfecting apparatus for a personal or individual dialysis equipment or system characterized in that the apparatus comprises a tank for holding electrolyzed hyperacidity water and a line for transporting electrolyzed hyperacidity water which extends from said tank to a line for supply of pure water in the personal dialysis system.

(5) This invention further provides a cleaning and disinfecting apparatus for hemodialysis equipment characterized in that the apparatus comprises
   (i) a tank for holding electrolyzed hyperacidity water and
   (ii) a line for transporting electrolyzed hyperacidity water which extends from said tank to at least one of (a) a dialysate B stock solution tank and (b) a line for supplying pure water for dilution of a dialysate stock solutions, with a solenoid valve being disposed in said line for transporting electrolyzed hyperacidity water.

Figure 3:
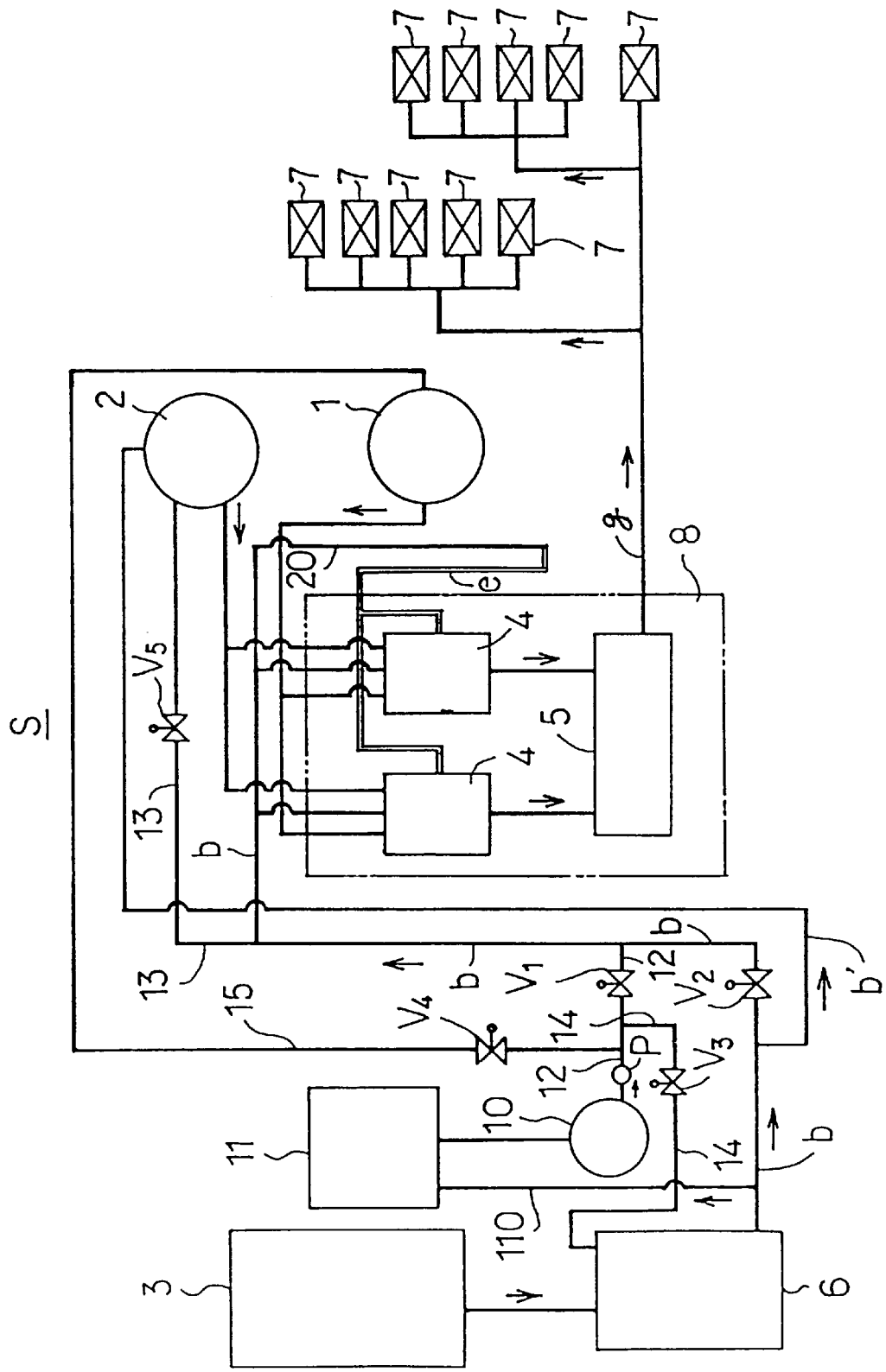
FIG. 3 is a schematic view showing a typical cleaning and disinfecting apparatus according to this invention on the multiple patient dialysis system.

(5a) Specifically, the present invention provides a cleaning and disinfecting apparatus for dialysis equipment characterized in that, as shown in FIG. 3, the apparatus comprises
   (i) a tank 10 for holding electrolyzed hyperacidity water,
   (ii) an electrolyzed hyperacidity water supply line 12 for transporting electrolyzed hyperacidity water from said tank 10 to a pure water supply line b for supplying pure water to a tank 4 for blending dialysate A and B stock solutions and diluting the mixture with pure water, the line 12 being connected to the pure water supply line b at a point downstream of the branching point at which a pure water supply branch line b' for supplying pure water to a dialysate 8 stock solution tank 2 branches out from said pure water supply line b, and
   (iii) a branch line 13 extending to the dialysate B stock solution tank 2 and branching Out from the pure water supply line b at a point downstream of the above connection between the electrolyzed hyperacidity water supply line 12 and the pure water supply line b and upstream of the tank 4 for blending dialysate A and B stock solutions and diluting the mixture with pure water, a solenoid valve V1 being disposed in the electrolyzed hyperacidity water supply line 12,
   a solenoid valve V5 being disposed in the branch line 13, and
   a solenoid valve V2 being disposed in the pure water supply line b at a point upstream of the above connection between the pure water supply line b and the electrolyzed hyperacidity water supply line 12

(6) The above cleaning and disinfecting apparatus described in (5a) may further comprise (iv) a line 14 for transporting electrolyzed hyperacidity water which extends from said tank 10 for holding electrolyzed hyperacidity water to a tank 6 for holding pure water, with a valve V3 being disposed in the same line 14, for opening and closing the line 14.

Figure 6:
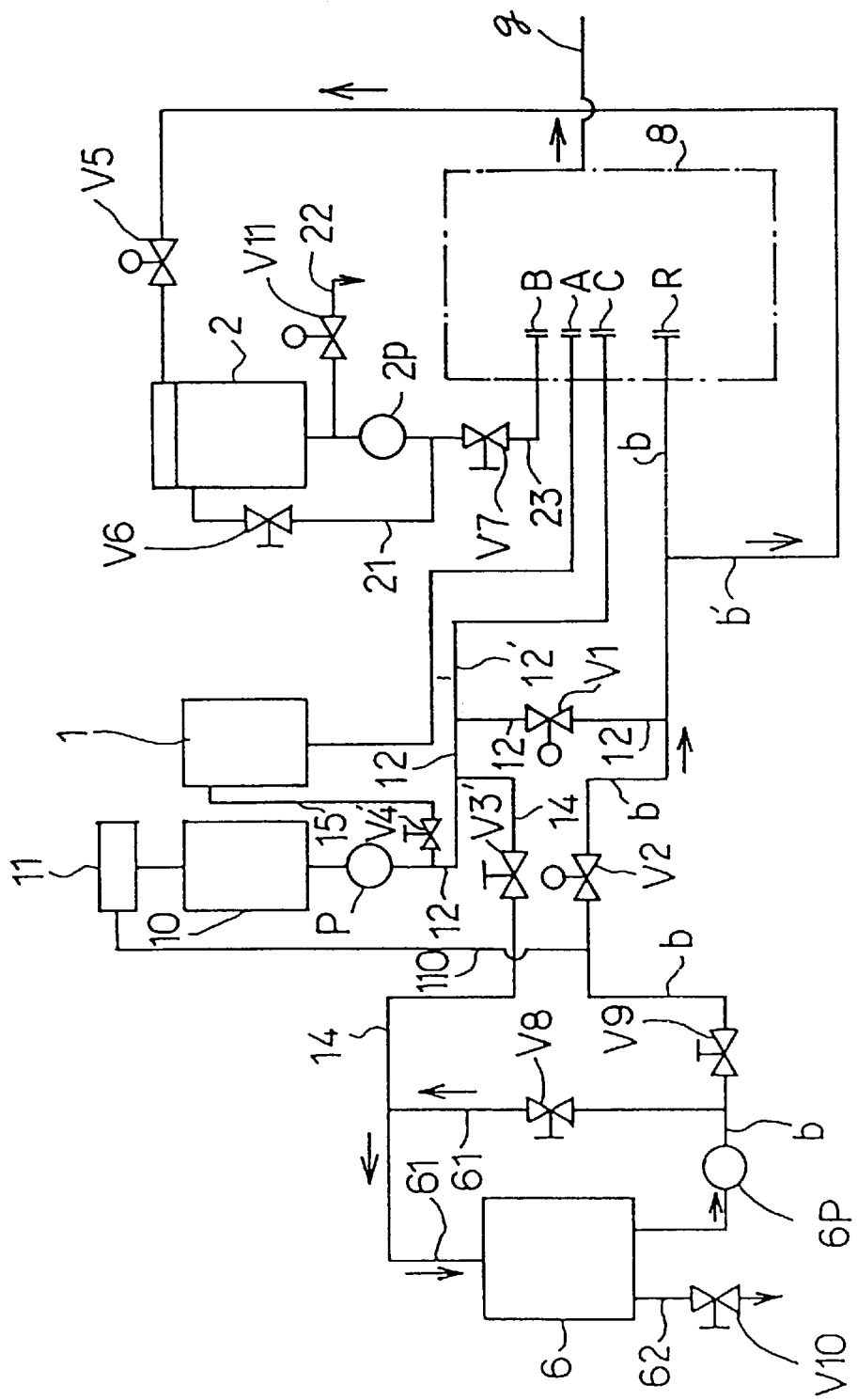
FIG. 6 is a schematic diagram illustrating another embodiment of the cleaning and disinfecting apparatus according to this invention on the multiple patient dialysis system.

(7) This invention further provides a cleaning and disinfecting apparatus for hemodialysis equipment or system characterized in that, as shown in FIG. 6, the apparatus comprises (i) a tank 10 for holding electrolyzed hyperacidity water,
   (ii) an electrolyzed hyperacidity water supply line 12 for transporting electrolyzed hyperacidity water from said tank 10 to a pure water supply line b for supplying pure water to a dialysate B stock solution tank 2, and optionally
   (iii) a line 14 for transporting electrolyzed hyperacidity water from said tank 10 to a tank 6 for holding pure water for dilution of dialysate stock solutions,
   a solenoid valve V1 being disposed in the electrolyzed hyperacidity water supply line 12 which is in communication with a pure water supply branch line b' for supply of pure water to a dialysate B stock solution tank 2, and
   a valve V3' being disposed in the line 14 for opening and closing the line 14.

(7a) Specifically, the cleaning and disinfecting apparatus as described above in (7) is characterized in that the apparatus comprises (i) a tank 10 for holding electrolyzed hyperacidity water, and
   (ii) a electrolyzed hyperacidity water supply line 12 for transporting electrolyzed hyperacidity water from said tank 10 to a pure water supply line b for supplying pure water to a tank 4 for blending the dialysate A and B stock solutions and diluting the mixture with pure water, said electrolyzed hyperacidity water supply line 12 being connected to the pure water supply line b at a point upstream of the branching point at which a pure water supply branch line b' for supplying pure water to a dialysate B stock solution tank 2 branches out,
   a solenoid valve V1 being disposed in the electrolyzed hyperacidity water supply line 12,
   a solenoid valve V5 being disposed in the pure water supply branch line b', and
   a solenoid valve V2 being disposed in the pure water supply line b at a point upstream of the connection between the pure water supply line b and the electrolyzed hyperacidity water supply line 12.

(8) The cleaning and disinfecting apparatus described in (7a) above may further comprise (iv) a line 14 for transporting electrolyzed hyperacidity water which extends from said tank 10 for holding electrolyzed hyperacidity water to a tank 6 for holding pure water, with a valve V3' being disposed in the same line 14, for opening and closing said line 14.

In the above description, the term "solenoid valve" is used in a broad sense of the term, including an "electrically operated valve". The same is true with the term used in the claims.

This invention is further described with reference to FIG. 3 which illustrates one embodiment of the invention (which applies to a multiple-patient dialysis system).

The dialysis system shown in FIG. 3 is similar to the conventional dialysis system shown in FIG. 12 except in the availability of cleaning and disinfecting means. Therefore, the like parts are indicated by the like reference symbols in FIGS. 3 and 12.

The dialysis system S is provided with a tank 10 for holding electrolyzed hyperacidity water.

Stored in this tank 10 is the electrolyzed hyperacidity water prepared in an electrolyzed hyperacidity water generating device 11 which is per se known. This device 11 is supplied with RO processed water from a tank 6 through a line 110 for the preparation of electrolyzed hyperacidity water. A valve (not shown) is disposed at the downstream end of the line 110 leading to the device 11.

A pipeline 12 for transporting electrolyzed hyperacidity water from said tank 10 includes a pump P disposed at the point of its origin. The line 12 communicates with at least a dialysate B stock solution tank 2 among the various components of dialysis system S. As shown in FIG. 3, this communication is established by connecting the line 12 to an intermediate position of a line b which supplies pure water (RO processed water) from tank 6 to tank 4 and connecting the tank 2 via a branch line 13 to the line b on the downstream side of the above connection between the line 12 and the line b. Namely, the branch line 13 branches out from the line b. at a point downstream of the connection between the line 12 and the line b and upstream of the tank 4.

The line 12 for transporting electrolyzed hyperacidity water is preferably in communication with the existing line e, too, via lines b and 20 and further to the pure water (RO processed water) tank 6. The reference numeral 14 in FIG. 3 indicates a line for this latter communication.

The line 12,may further be connected to the dialysate A stock solution tank. The reference numeral 15 indicates a line for this communication.

The line 12 is provided with stop valve V1, the line b with stop valve V2, the line 14 with stop valve V3, the line 15 with stop valve V4, and the line 13 with stop valve V5. These stop valves may be solenoid valves.

As shown in FIG. 4, the tank 2 is preferably equipped with a water level sensor switch 18 for setting a high water level and a water level sensor switch 19 for setting a low water level so that the tank may hold the dialysate B stock solution between the levels throughout a dialysis session.

Upon completion of an extracorporeal hemodialysis session, the dialysis system S is post-rinsed in the conventional manner. Then, the tanks 2, 4 and 5, the console 7, line g interconnecting tank 5 and console 7, and the lines downstream of the console are cleaned and disinfected with the electrolyzed hyperacidity water from said tank 10. Switching from this post-rinse mode to a cleaning and disinfection mode is effected by opening of said stop valves V1, V4 and V5 in response to a command signal from the dialysate supply unit (central) 8.

Figure 5:
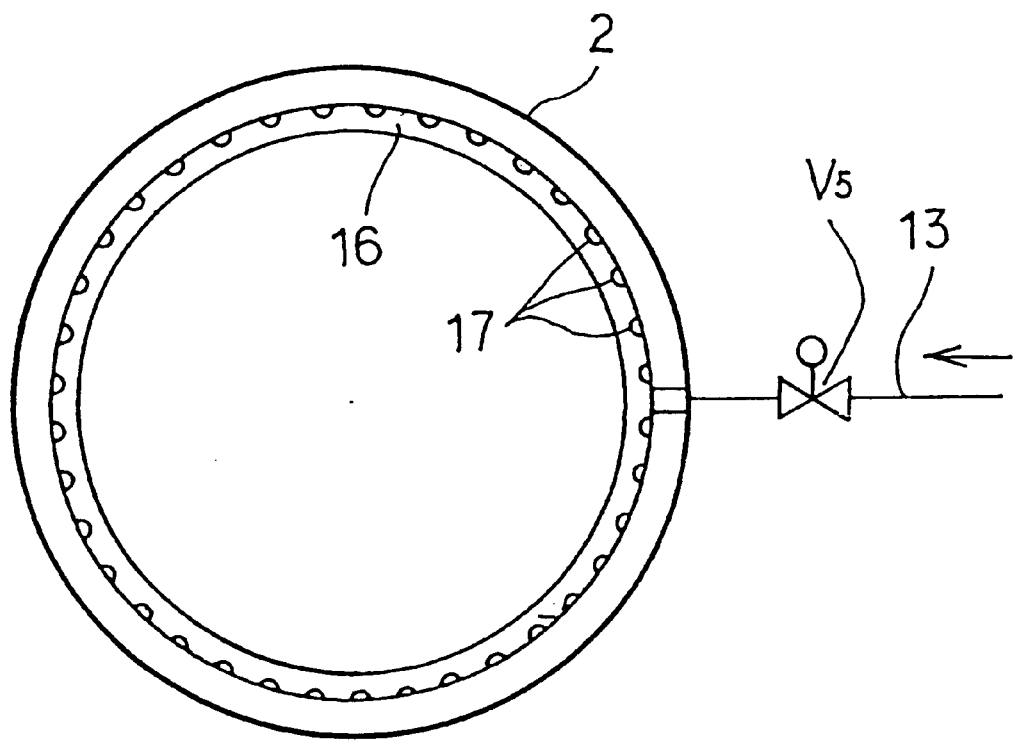
FIG. 5 is a transverse section view of the tank shown in FIG. 4.

The cleaning and disinfection of tank 2 with electrolyzed hyperacidity water is preferably carried out in the manner illustrated, for example, in FIGS. 4 and 5, where the inner wall of tank 2 is intensively flushed by a shower 16.

The shower 16 is ring-shaped and its nozzle orifices 17 are directed toward the inner wall of the tank 2.

In case the line 12 is also in communication with the existing line e, the tank 4 is also supplied with electrolyzed hyperacidity water from the line e. Therefore, even where it is so arranged that the dialysate blending operation will not be started unless the tank 4 is filled with a certain quantity of liquid (which is the common arrangement), the blending operation is initiated in the tank 4 so that the cleaning and disinfection is effected with the supplied electrolyzed hyperacidity water.

The tank 5 is cleaned and disinfected with the electrolyzed hyperacidity water from tank 4. Line g, console 7, and the lines downstream of the console 7 are cleaned and disinfected with electrolyzed hyperacidity water from tank 4.

In the case where the pure water (RO processed water) tank 6 is in communication with line 12, this tank 6 can also be cleaned and disinfected. In the case where the tank 1 is in communication with line 12, this tank 1 can also be cleaned and disinfected.

FIG. 6 shows another embodiment of this invention which is pertinent to a multiple-patient dialysis system. In FIGS. 6 and 3, the like parts are indicated by the like reference symbols.

The embodiment shown in FIG. 6 is substantially identical to the embodiment shown in FIG. 3 except that branch line b' is used in place of the branch line 13 shown in FIG. 3, that valve V3 in line 14 shown in FIG. 3 is a needle valve V3', that valve V4 in line 15 shown in FIG. 3 is a needle valve V4', that line 12 is connected to central 8 via branch line 12' as well, that lines e and 20 are omitted, and that dialysate B stock solution tank 2 is provided with a return line 21 including a valve V6, e.g. a needle valve.

This embodiment has the advantage of eliminating the need for the branch line 13 shown in FIG. 3, since the electrolyzed hyperacidity water can be transported to the dialysate 8 stock solution tank 2 through the existing branch line by conventionally provided.

The downstream end of branch line 12' may be connected to the conventional disinfectant inlet of central 8 (FIG. 6) when such inlet for introducing conventional disinfectant is provided with the dialysis equipment.

In FIG. 6, the console and the water treatment unit are not shown.

In FIG. 6, indicated at 22 is a drain pipe for tank 2, and 2P represents a pump for tank 2. V7 represents a needle valve in line 23 for dialysate B stock solution from tank 2. V8 represents a needle valve in a return line 61 to RO processed water tank 6. V9 is a needle valve disposed in line b (extending from RO processed water tank) at a point downstream of a water feed pump 6P for said tank 6. V10 is a needle valve in a drain pipe 62 of RO processed water tank 6. These components are per se known and can be the existing components. It is preferable that the drain pipe 22 of dialysate B stock is solution tank 2 is provided with a valve V11, which is preferably a solenoid valve.

Also referring to FIG. 6, reference symbol A shown in the central 8 represents an inlet for the dialysate A stock solution; B represents an inlet for the dialysate B stock solution; C represents an inlet for the cleaning disinfectant (electrolyzed hyperacidity water), which inlet can be an inlet for introducing conventional cleaning disinfectant, if such inlet for conventional cleaning disinfect is already provided; and R represents an inlet for RO processed water.

The equipment shown in FIG. 6 is cleaned and disinfected in the same manner as the equipment shown in FIG. 3.

Figure 7:
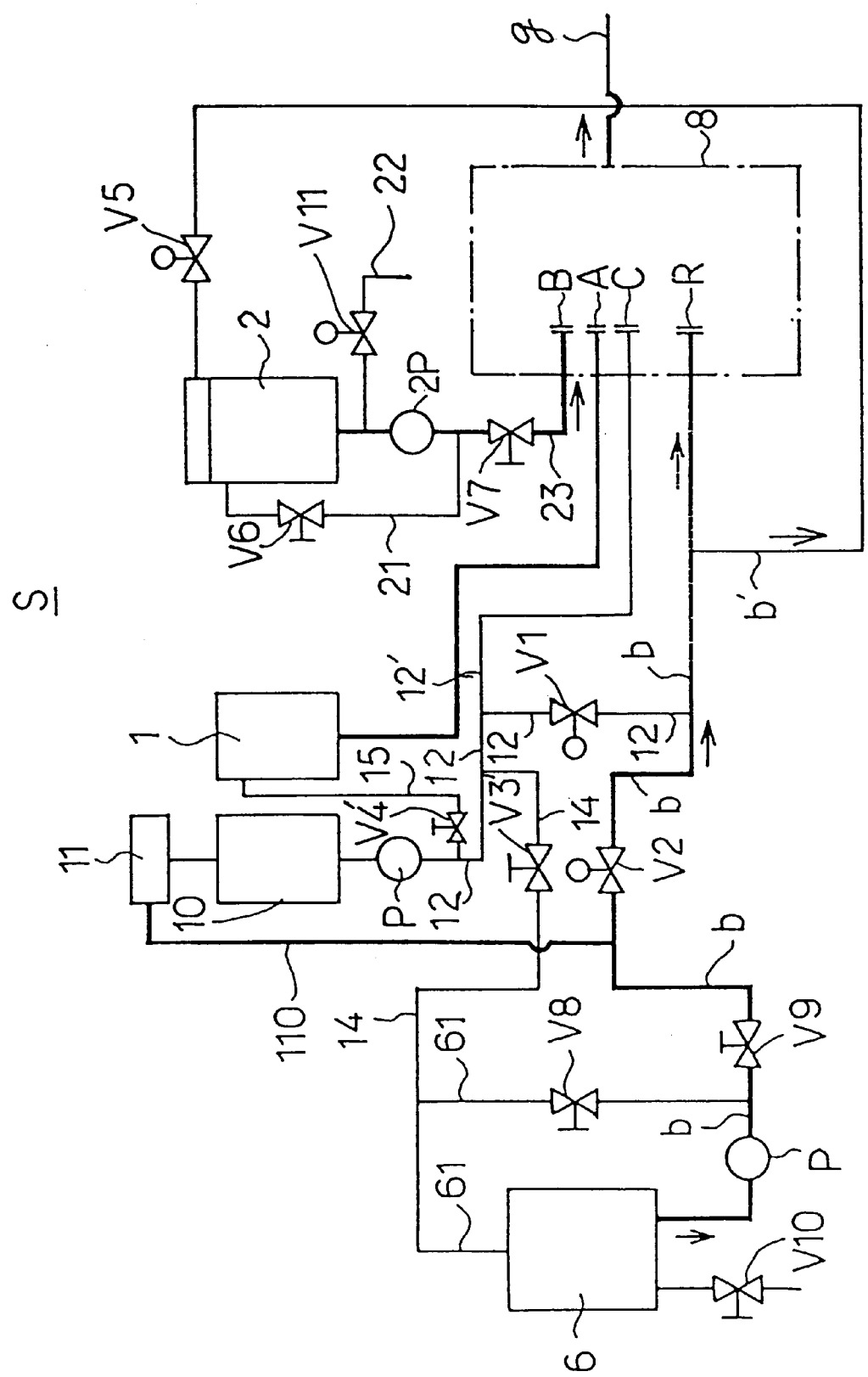
FIG. 7 is a diagrammatic representation of the dialysis session employing the cleaning and disinfecting apparatus of the invention shown in FIG. 6.
Figure 8:
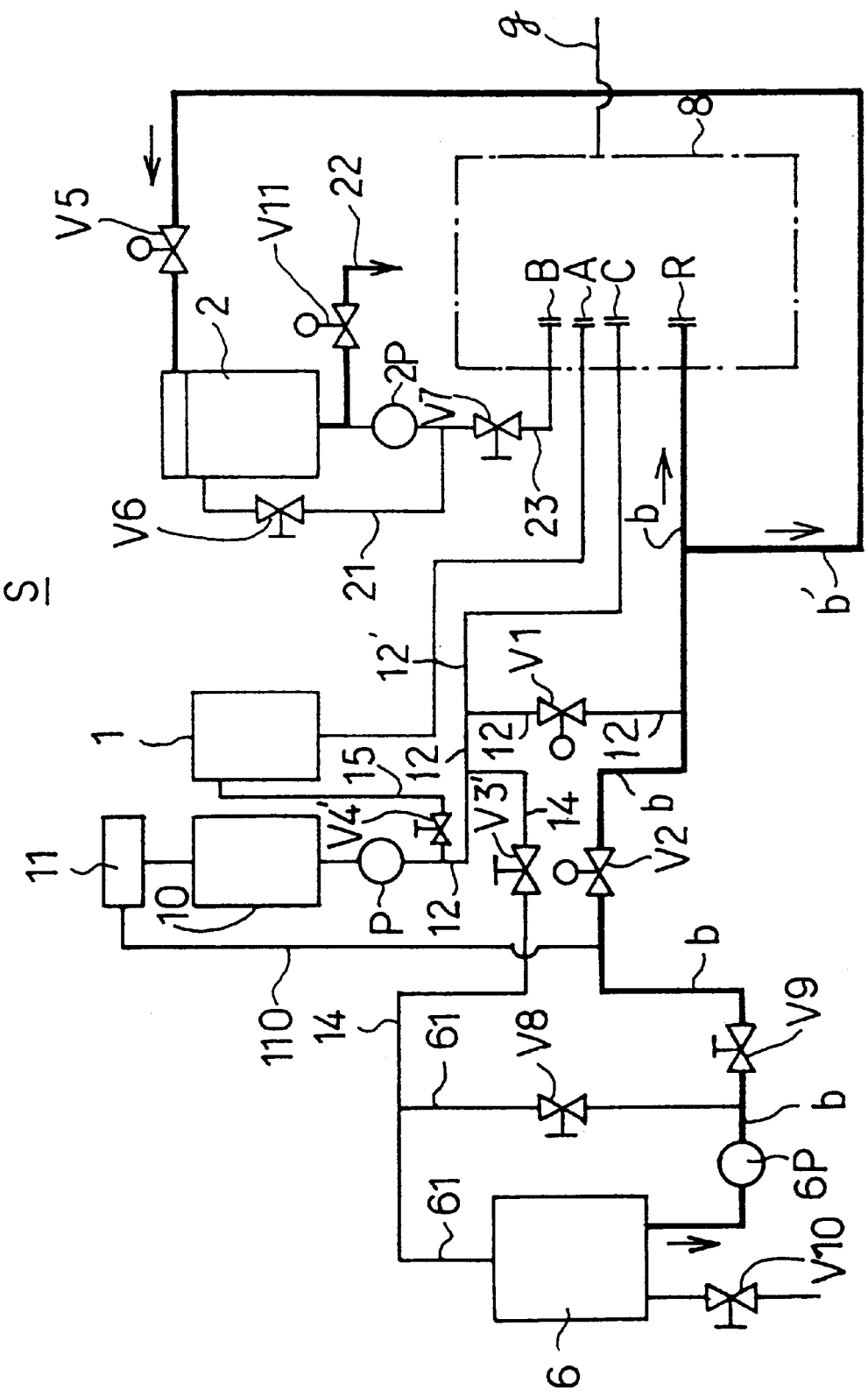
FIG. 8 is a diagrammatic representation of the rinse session using the cleaning and disinfecting apparatus of the invention shown in FIG. 6.
Figure 9:
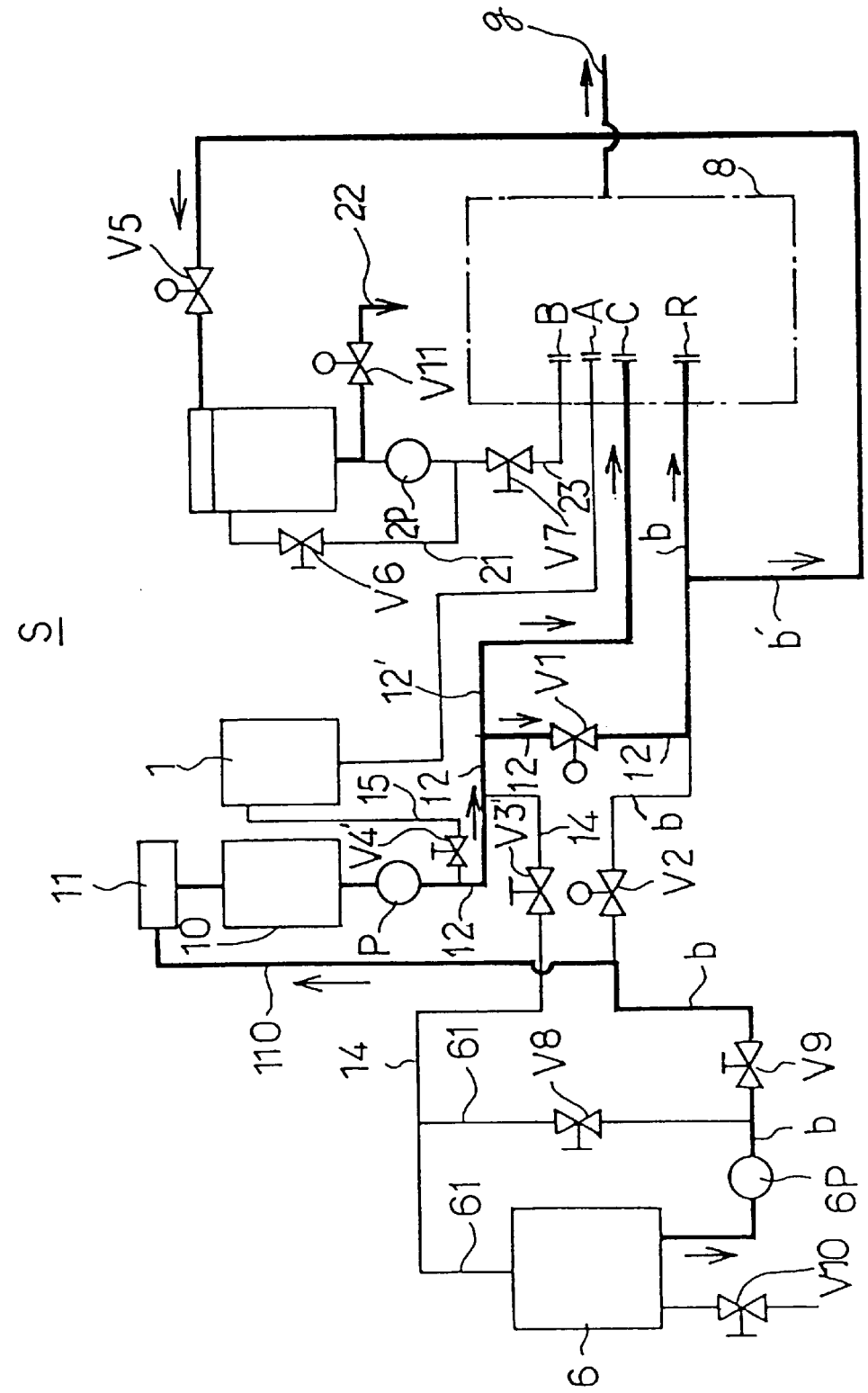
FIG. 9 is a diagrammatic representation of the cleaning and disinfecting session using the cleaning and disinfecting apparatus of the invention shown in FIG. 6.
Figure 10:
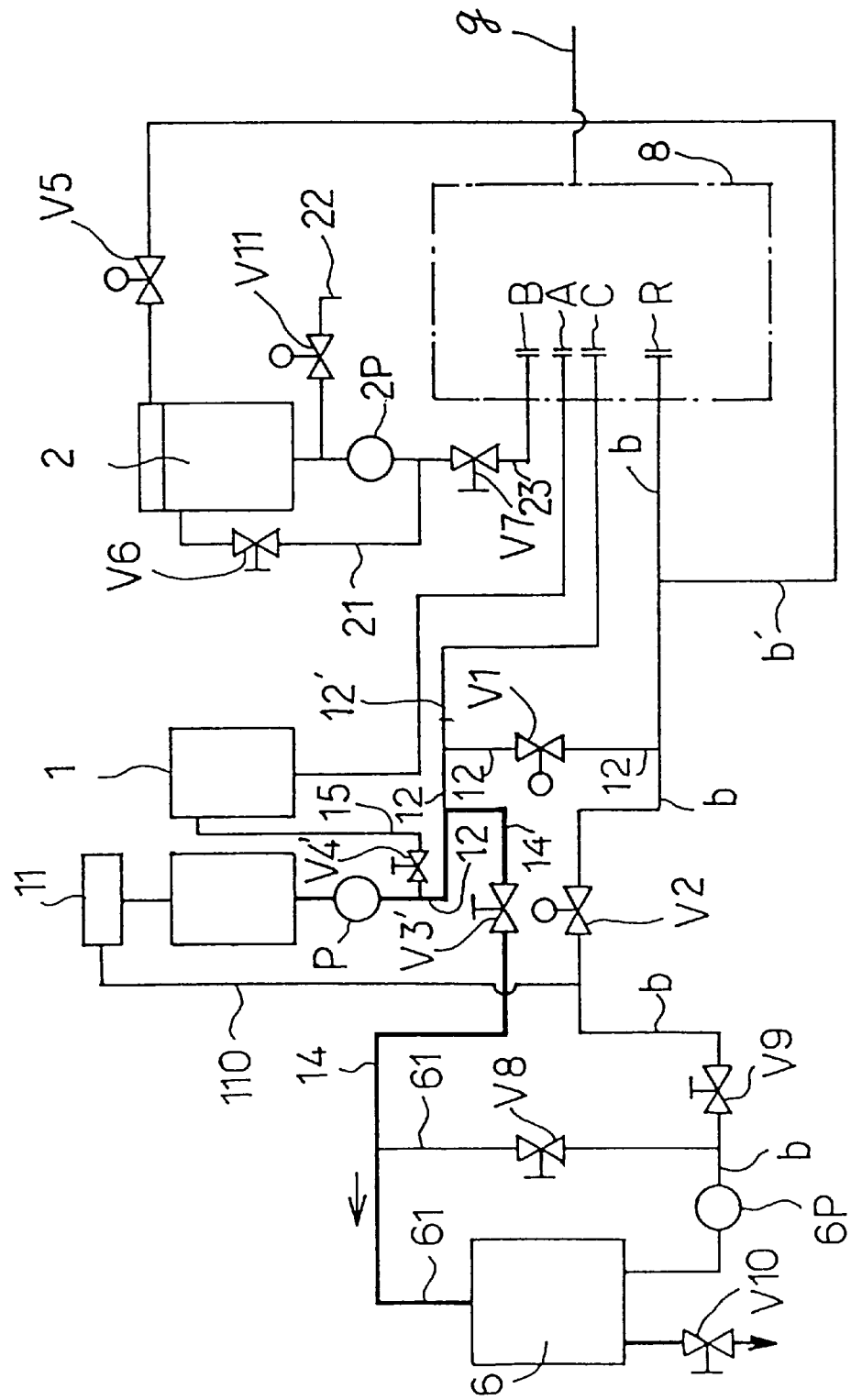
FIG. 10 is a diagrammatic representation of the process of cleaning and disinfecting the RO processed water tank using the cleaning and disinfecting apparatus of the invention illustrated in FIG. 6.

Referring to the dialysis, rinse (post-rinse and pre-rinse), cleaning and disinfection (except for RO processed water tank), and RO processed water tank cleaning and disinfection modes in the dialysis system provided with the cleaning and disinfecting apparatus of this invention, the corresponding statuses of the respective lines and valves are shown in FIG. 7 (dialysis on), FIG. 8 (rinse on), FIG. 9 (cleaning and disinfection on), and FIG. 10 (RO processed water tank cleaning and disinfection on). In FIGS. 7 through 10, the pipelines indicated by bold lines are ON with the valves in these lines remaining open and with the pump(s) in these lines kept operating. The lines not operating are indicated by fine lines. The valves in these lines remain closed.

In the rinse mode (FIG. 8), the solenoid valve V11 in the drain pipe 22 of dialysate B stock solution tank 2 remains open for a certain time after the start of rinse and, then, closes. The open valve time is set with a timer. During this rinse mode, a valve (not shown) disposed at a downstream and of line 110 remains closed.

In the cleaning and disinfection mode (FIG. 9), too, the valve V11 (which is preferably a solenoid valve) in the drain pipe 22 remains open for a certain time after the start of cleaning and disinfection and, then, closes. The open valve time is set with a timer.

During the cleaning and disinfection of RO processed water tank 6 (FIG. 10), the power sources (not shown) for the water treatment until and dialysate supply unit (central) 8 are OFF. In this mode, the valves in the lines (other than valves V3' and V10) and a solenoid valve (not shown) at the cleaning disinfectant inlet c of the central 8 remain closed. The RO processed water tank 6 is supplied with electrolyzed hyperacidity water by opening the needle valve V3'.

The electrolyzed hyperacidity water for this purpose is the same as the electrolyzed hyperacidity water described in connection with cleaning and disinfecting method.

The post-rinse is conventionally carried out over a long time for driving out the residual dialysate and the organic matter which might detract from the effect of disinfection from the pipelines and flushing out bacteria and endotoxins, but since the cleaning and disinfection operation is carried out with electrolyzed hyperacidity water in this invention, the eliminating or inactivating effect on bacteria and endotoxins is so high that both the quantity of rinse water and the post-rinse time are reduced to about ¼–⅔ or about ¼–½ as compared with the conventional technology.

Moreover, since the line 12 for transporting electrolyzed hyperacidity water from the electrolyzed hyperacidity water tank 10 is in communication with the dialysate B stock solution tank 2 in this invention, not only the tank 4 and the location downstream of the tank 4 but also the location upstream of tank 4 can be cleaned and disinfected to effectively remove bacteria and inactivate endotoxins.

Figure 11:
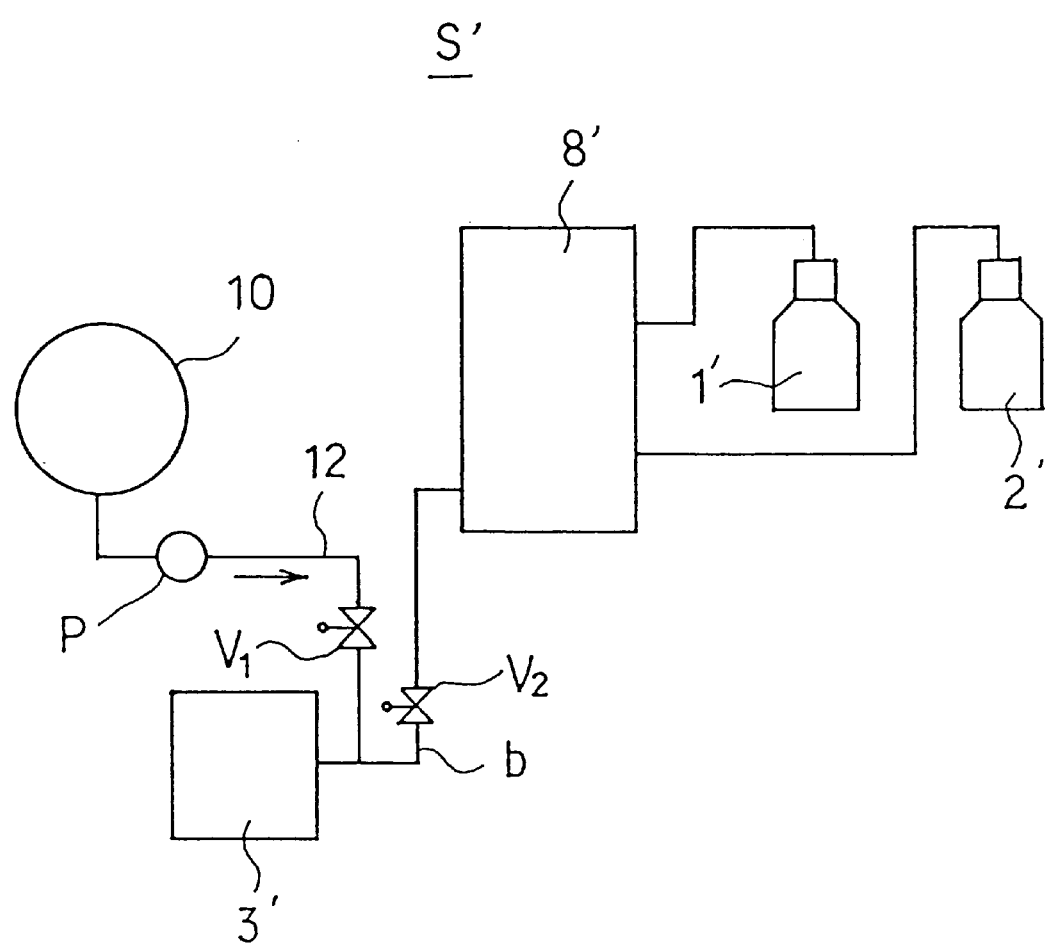
FIG. 11 is a schematic diagram illustrating a typical cleaning and disinfecting apparatus according to this invention on the personal dialysis system.

This invention can be applied to a personal or individual dialysis system or equipment, too. This mode of use is illustrated in FIG. 11. The personal dialysis system shown in FIG. 11 is per se similar to the conventional personal dialysis system. In FIGS. 11 and 3, the like parts are indicated by the like reference symbols.

The personal dialysis system S' is not provided with tanks 4 and 5 which exist in the central described hereinbefore instead, there are viscous chambers which are respectively actuated by a viscous pump to aspirate and mix dialysate A and B stock solutions and pure water and to supply the dialysate so prepared to the blood dialyzer. Two viscous chambers are provided and alternatingly driven to continuously perform the above-mentioned supply of the dialysate. In FIG. 11, the viscous chambers, viscous pump, etc. are globally indicated as block 8'.

In FIG. 11, indicated at 1' is a dialysate A stock solution tank; at 2', a dialysate B stock solution tank; and at 3', a water treatment unit similar to the unit described with reference to FIG. 3 or FIG. 12 for the preparation of diluent pure water (RO processed water).

In the case of the personal dialysis system S', too, the dialysis system S' is provided with an electrolyzed hyperacidity water tank 10. Electrolyzed hyperacidity water, produced in the same manner as in the equipment shown in FIG. 3 or FIG. 6, is stored in the above tank 10. The line 12 for electrolyzed hyperacidity water as extending from tank 10 is connected to line b for feeding diluent pure water (RO processed water) from the water treatment unit 3' to the viscous chambers in the block 8'. This line 12 is provided with a pump P at its origin.

Also in the system shown in FIG. 11, the dialysis session is followed by post-rinse of dialysis system S' which, in turn, is followed by the cleaning and disinfection of dialysis system S' with electrolyzed hyperacidity water from tank 10, just as in the system shown in FIG. 3 or FIG. 6. The target locations of this cleaning and disinfecting procedure are the line b, the viscous chambers (which correspond to the tank 4 in FIGS. 3 and 6) or the like, within the block 8'.

Thus, in the personal dialysis system S', too, the endotoxins and bacteria are cleaned and disinfected at not only the location corresponding to the tank for diluting and blending dialysate A and B stock solutions but also the location upstream thereof.

In the system shown in FIG. 11, switching from the post-rinse mode to the cleaning and disinfection mode can be effected in the same manner as described with reference to FIGS. 3 and 6.

As can be seen from FIGS. 3, 6 and 11, the cleaning and disinfection according to this invention can be accomplished without modifying the existing dialysis system or only with minor modifications such as installation of solenoid valves or stop valves in the pipelines.

Furthermore, as will be apparent from the foregoing description of the dialysis, rinse, cleaning and disinfection, and RO processed water tank cleaning and disinfection modes for the dialysis system provided with the apparatus of this invention and the corresponding illustrations presented in FIGS. 7 through 10, the cleaning and disinfection of the dialysis system can he carried out whenever necessary without reassembling the pipelines of the dialysate circuit etc. Thus, the apparatus of this invention can be efficiently applied to the cleaning and disinfection of a dialysis system and lends itself well to automatic execution of the cleaning and disinfecting operation. The apparatus is also adaptable to automatic switchover from a post-rinse mode to a cleaning and disinfection mode.

Thus, in accordance with this invention, not only the tank in the dialysate supply unit (central) where dialysate A and B stock solutions are blended and diluted or the location corresponding to said tank and the location downstream thereof but also the location upstream thereof can be cleaned and disinfected to get rid of bacteria and to inactivate endotoxins and, moreover, such cleaning and disinfection can be achieved without modifying the existing dialysis system or only with minor modifications.

The invention further provides a cleaning and disinfecting apparatus for dialysis equipment, which can be efficiently applied to the cleaning and disinfection for removal or inactivation of bacteria and endotoxins and adapted to automatic cleaning and disinfection.

EXAMPLES

The following examples and test examples are intended to describe this invention in further detail and should by no means be construed as defining the scope of the invention.

EXAMPLE 1

(a) Production of electrolyzed hyperacidity water Using an electrolyzed hyperacidity water generator, an electrolyzed hyperacidity water having a pH value of 2.4 and a redox potential of 1155 mV was prepared.

The electrolyzed hyperacidity water thus obtained was used as the cleaning disinfectant for dialysis equipment in the following experiment.

(b) Time courses of pH and redox potential at the terminal end of a dialysate circuit.

In a multiple-patient dialysis equipment for 30 patients, the electrolyzed hyperacidity water obtained under (a) was fed from the dialysate supply unit to the dialysate lines of 30 bedside patient monitors to investigate the tino courses of its pH and redox potential.

Thus, at the end of a dialysis session, a post-rinse was performed for 30 minutes. After completion of the post-rinse, the rinse water was drained off from the tank within the dialysate supply unit. The supply tank of the dialysate supply unit was filled with the above electrolyzed hyperacidity water up Lo capacity, and this electrolyzed hyperacidity water was distributed via the pipeline to one of the 30 patient monitors which was remotest from the dialysate supply unit At this terminal monitor, the coupler (to the joint of the dialyzer on the dialysate side) was disconnected and the electrolyzed hyperacidity water was allowed to flow out using care not to touch the coupler joint.

The electrolyzed hyperacidity water was fed at ambient temperature and a flow rate of 500 ml/minute per patient monitor.

During a period of 20 minutes after the start of feeding of electrolyzed hyperacidity water, the electrolyzed hyperacidity water flowing out from the coupler joint was sampled every minute and the pH and redox potential (mV) of each sample was immediately determined with a portable pH meter HM-14P (Toa Dempa Kogyo Kabushiki Kaisha).

The results are shown in Table 1.

TABLE 1

| Time in minutes | pH | Redox potential (mV) |
| --- | --- | --- |
| 0 | 6.54 | 643 |
| 1 | 6.68 | 627 |
| 2 | 6.65 | 617 |
| 3 | 3.09 | 1063 |
| 4 | 2.45 | 1150 |
| 5 | 2.46 | 1153 |
| 6 | 2.44 | 1154 |
| 7 | 2.44 | 1155 |
| 8 | 2.44 | 1155 |
| 9 | 2.43 | 1156 |
| 10 | 2.43 | 1156 |
| 11 | 2.43 | 1156 |
| 12 | 2.43 | 1156 |
| 13 | 2.42 | 1156 |
| 14 | 2.46 | 1156 |
| 15 | 2.42 | 1156 |
| 20 | 2.42 | 1150 |

It is apparent from Table 1 that the pH and redox potential of electrolyzed hyperacidity water reached effective levels in about 4 minutes following the start of feeding and, thereafter, maintained substantially constant values. Thus, after this 4-minute period, the pH and redox potential of electrolyzed hyperacidity water were sustained even at the terminal end of the dialysate line, indicating that an electrolyzed hyperacidity water of high potential can be consistently supplied.

(c) Time courses of endotoxin concentration and bacterial population at the terminal end of the dialysate circuit Under the same conditions as (b) above, the electrolyzed hyperacidity water flowing out from the coupler joint of the terminal monitor was sampled every minute over 20 minutes from the start of feeding of the electrolyzed hyperacidity water, and each sample was placed in a specified container and preserved in the refrigerator (4° C.). Then, the concentration of endotoxins and the number of bacteria in each sample were determined.

The number of bacteria was determined by the general bacteriological method (plate diffusion assay). The endotoxin concentration was estimated by the endospecy method.

The results are shown in Table 2.

TABLE 2

| Time in minutes | Endotoxin (pg/ml) | Bacteria | Bacterial population (cfu/ml) |
|---|---|---|---|
| 0 | 14.8 | (1) | 3.7 × 100 |
|   |      | (2) | 2.0 × 10 |
|   |      | (3) | 3.6 × 100 |
| 1 | 4.1  | (3) | 7.0 × 10 |
| 2 | 4.1  | ND  | — |
| 3 | <1.0 | ND  | — |
| 4 | <1.0 | ND  | — |
| 5 | <1.0 | ND  | — |
| 6 | <1.0 | ND  | — |
| 7 | 1.1  | ND  | — |
| 8 | <1.0 | ND  | — |
| 9 | <1.0 | ND  | — |
| 10 | <1.0 | ND | — |
| 11 | <1.0 | ND | — |
| 12 | <1.0 | ND | — |
| 13 | <1.0 | ND | — |
| 14 | <1.0 | ND | — |
| 15 | <1.0 | ND | — |
| 20 | <1.0 | ND | — |

(1) Corynebacerium sp.
(2) *Pseudomonas stutzeri*
(3) Pseudomonas 5p.
ND: not detected It is apparent from Table 2 that after the initial 2-minute period the endotoxin concentration as determined by said endospecy method was not higher than 1.0 pg/ml and no bacteria were detected.

(d) Endotoxins and bacteria in other locations

The endotoxin concentrations and bacterial counts in other parts of the above dialysis equipment were determined by the same methods as used under (c).

Thus, using (1) a tap water sample obtained after 10 minutes of free issue from a faucet in the dialysis room, (2) a sample of RO processed water obtained after 10 minutes of issue from the water supply port of the line interconnecting the reverse osmosis device and the dialysate B tank, (3) a commercial physiological saline solution (tradename: Physiological Saline, product of Otsuka Pharmaceutical Co., Ltd.), and (4) a commercial infusion fluid (tradename: "HF-SOLITA", Shimizu PharmaceuLical Co., Ltd.), the endotoxin concentration and bacterial count were determined. The results are shown in Table 3.

With regard to the physiological saline solution and infusion fluid, each product bottle was hung on a drip infusion stand and, after the cover was removed using care not to touch the rubber stopper, the content was aspirated into a syringe. The sample was immediately transferred to a specified container and preserved in the refrigerator till use.

TABLE 3

| Location: | Endotoxin (pg/ml) | Bacteria | Bacterial population (cfu/ml) |
|---|---|---|---|
| Tap water | 229.5 | ND | — |
| RO processed water | 36.2 | ND | — |
| Physiological saline | <1.0 | ND | — |
| Infusion fluid | <1.0 | ND | — |

ND: not detected

It is not conceivable that bacteria should ever be detected in tap water (under the water quality standard of the Water Supply Law). However, there is no comparable standard on endotoxin and partly for this reason, the endotoxin concentration of tap water was fairly high. RO processed water inherently shows low endotoxin levels (0–10 pg/ml but the fairly high value found was probably due to aging of the membrane. Neither endotoxins nor bacteria should be found in any physiological salt solution or infusion. As assayed by the endospecy method, the endotoxin data (Table 3) were also less than 1.0 pg/ml.

The results presented in Tables 2 and 3 indicate that the use of the cleaning disinfectant of this invention, namely electrolyzed hyperacidity water, results not only in the elimination of bacteria but also in the reduction of endotoxin concentration to low levels comparable to those found in physiological saline and infusions.

Test Example 1

(a) In a multiple-patient dialysis equipment for 30 patients, a dialysis session was followed by the conventional post-rinse of the dialysate circuit. Upon completion of the post-rinse, the rinse water in the tank of the dialysate supply unit was withdrawn. Then, the supply tank of the dialysate supply unit was filled with a cleaning disinfectant up to capacity and the disinfectant was distributed to the 30 patient monitors via distribution lines at room temperature. The cleaning disinfectant was allowed Lo stand within the pipelines overnight. The following morning, the cleaning disinfectant was driven out with water. The above procedure was repeated for 6 consecutive days.

As the above cleaning disinfectant, the following three different cleaning disinfectants were used.

(1) Electrolyzed hyperacidity water prepared by the method described in Example 1 (a) (every day for 6 days)

(2) Sodium hypochlorite aqueous solution (day 1 and days 3–5)+acetic acid aqueous solution (day 2 and day 6)
Concentration of sodium hypochlorite aqueous solution=0.02 wt. %
Concentration of acetic acid aqueous solution=1 wt. %

(3) Sodium hypochlorite aqueous solution (day 1 and days 3–5)+acetic acid aqueous solution (day 2 and day 6)+formalin (day 1)
Concentration of sodium hypochlorite aqueous solution=0.02 wt. %
Concentration of acetic acid aqueous solution=1 wt. %
Concentration of formalin=3.8 wt. %

The post-rinse after the dialysis session was carried out with RO processed water at a flow rate of 500 ml/min. per patient monitor. The rinse time was 30 minutes when the cleaning disinfectant (1) of this invention was to be used, or 60 minutes where the conventional cleaning disinfectant (2) or (3) was to be used.

Each cleaning disinfectant was fed at a rate of 500 ml/min. per patient monitor. The duration of feeding was as follows.

Line (1)

Electrolyzed hyperacidity water: 20 min

Line (2)

Sodium hypochlorite aqueous solution: 45 min.

Acetic acid aqueous solution: 45 min.

Line (3)

Sodium hypochlorite aqueous solution: 45 min.

Acetic acid aqueous solution: 45 min.

Formalin: 77 liters fed and left to stand in the line for 12–15 hours, followed by rinse with water for 2.5 hours.

The rinse (pre-rinse which is carried out prior to dialysis) for flushing out the cleaning disinfectant after its overnight standing was carried out with RO processed water at a flow rate of 500 ml/min. per patient monitor for 30 minutes with respect to line (1) or for 60 minutes with respect to lines (2) and (3).

Since it was difficult to determine the endotoxin concentration and bacterial count in the cleaning solutions (2) and (3), the endotoxin concentration and bacterial count in the RO processed water used in the rinse immediately prior to the completion of pre-rinse before the dialysis session were determined by the same method as used in Example 1, and the relative effectiveness of the respective cleaning disinfectants was evaluated.

The method of sampling the above RO processed water was as follows. Thus, from each of the 6 terminal patient monitors of the above-mentioned 30-patient dialysis equipment (consoles 5 and 15 for cleaning disinfectant (1) (electrolyzed hyperacidity water), consoles 1 and 6 for cleaning disinfectant (2), and consoles 20 and 28 for cleaning disinfectant (3)), the coupler was disconnected 10 minutes before completion of the pre-rinse and, with the coupler joint remaining on, the RO processed water used in the rinse was allowed to flow out for 5 minutes and collected directly in a specified container.

In other words in the case of cleaning disinfectant (1) (electrolyzed hyperacidity water), the coupler was disconnected after 20 minutes of pre-rinse and the RO processed water used in the rinse was allowed to flow out for 5 minutes and, then, collected.

In the case of cleaning disinfectants (2) and (3), the coupler was disconnected after 50 minutes following the start of pre-rinse and the RO processed water used in the rinse was allowed to flow out for 5 minutes and, then, collected.

The measured ondotoxin concentrations are shown in Table 4. The endotoxin concentration given in Table 4 is the mean of 6 experiments (day 1–day 6).

TABLE 4

| Cleaning disinfectant | Console No. | Endotoxin (pg/ml) |
| --- | --- | --- |
| Electrolyzed hyperacidity water | 5 | 1.1 ± 1.1 |
|  | 15 | 1.1 ± 1.1 |
| Sodium hypochlorite + acetic acid | 1 | 162.4 ± 61.2 |
|  | 6 | 162.8 ± 51.9 |

TABLE 4-continued

| Cleaning disinfectant | Console No. | Endotoxin (pg/ml) |
| --- | --- | --- |
| Sodium hypochlorite + acetic acid + formalin | 20 | 5.9 ± 6.5 |
|  | 28 | 4.4 + 4.9 |

The results of the 1st through 6th (days 1–6) bacteriological examinations are shown in Table 5.

TABLE 5

| Cleaning disinfectant | Console | Disinfection | | | | | |
| --- | --- | --- | --- | --- | --- | --- | --- |
|  |  | 1st | 2nd | 3rd | 4th | 5th | 6th |
| Electrolyzed hyperacidity water | 5 | ND | ND | ND | ND | ND | ND |
|  | 15 | ND | ND | ND | ND | ND | ND |
| Sodium hypochlorite + acetic acid | 1 | ND | ND | ND | ND | ND | ND |
|  | 6 | ND | ND | ND | ND | ND | ND |
| Sodium hypochlorite + acetic acid + formalin | 20 | ND | (A) | ND | ND | ND | ND |
|  | 28 | ND | ND | ND | ND | ND | ND |

(A): *Acinetobacter calcoaceticus*
ND: not detected

It is apparent from Tables 4 and 5 that with the conventional disinfectants ((2) and (3)), no bacterial growth was found except in one location and the results were fairly satisfactory on the whole. However, the endotoxin concentration was fairly high with cleaning disinfectant (2) and relatively high with cleaning disinfectant (3) as well.

On the other hard, when electrolyzed hyperacidity water (1), i.e. the cleaning disinfectant of this invention, was employed, endotoxins could be sufficiently eliminated or inactivated, not to speak of complete removal of bacteria.

It is, therefore, clear that the cleaning disinfectant of this invention, namely electrolyzed hyperacidity water, is more effective than the conventional disinfecting agents, i.e. sodium hypochlorite, acetic acid and/or formalin.

Test Example 2

In the same 30-patient dialysis equipment as used in Test Example 1, the quantity of RO processed water used in the cleaning and disinfection and rinse procedures for a month was evaluated under the following conditions.

(1) The number of patient monitors (consoles): 30

(2) The cleaning disinfection mode: once a day and 25 times a month (3) Recovery of RO processed water from tap water: 65%

(4) The flow rate of rinse water and cleaning disinfectant per patient monitor: 500 ml/min.

However, since the sodium hypochlorite solution and other conventional disinfectants are solutions of low concentration, each of them was assumed to be 100% water. The electrolyzed hyperacidity water of this invention was also virtually water, it was similarly assumed to be 100% water.

(a) The cleaning and disinfection method using the conventional disinfectants, i.e. sodium hypochlorite, acelic acid and/or formalin, generally requires 60 minutes for post-rinse after dialysis, 30 minutes for cleaning and disinfection, and 60 minutes for pre-rinse before the next dialysis, or a total of 150 minutes.

The daily water consumption per patient monitor (console) is (500 ml/min.)×150 (min.)=75 liters. Therefore, the total daily water consumption for 30 consoles is 2250 liters. Since the recovery rate of RO processed water is 65%, the daily tap water consumption is 250÷0.65=ca. 3461 liters. Multiplying this quantity by 25 gives a monthly consumption of about 86.5 m$^3$.

(b) When electrolyzed hyperacidity water is used in accordance with this invention, the post-rinse time can be reduced to 30 minutes, the cleaning and disinfection time is 20 minutes, and, because of the safety of electrelyzed hyperacidity water, the pre-rinse time is 30 minutes. The total time is 80 minutes.

Therefore, the monthly tap water consumption is (500 ml/min.)×80 (min.)=40 liters per console or 1200 liters for 30 consoles. Since the recovery rate of RO processed water is 65%, the daily tap water requirement is 1200÷0.65=ca. 1846 liters. Multiplying this quantity by 25 gives a monthly tap water consumption of about 46.2 m$^3$.

(c) Therefore, when the cleaning disinfectant of this invention, namely electrolyzed hyperacidity water, is employed, the monthly tap water consumption is reduced to about one-half, thus providing for a drastic decrease in water consumption compared with the conventional technology. Moreover, the rinse time and cleaning and disinfecting time are also reduced so that this invention contributes considerably to cost reduction and operation efficiency.

Furthermore, since this invention does not involve the use of toxic substances such as sodium hypochlorite and formalin, the invention is advantageous in terms of safety as well.

What is claimed is:

1. An apparatus for cleaning and disinfecting hemodialysis equipment, wherein the apparatus comprises:
   hemodialysis equipment comprising
      a dialysate supply unit,
      a tank for holding pure water connected to said dialysate supply unit,
      a dialysate B stock solution tank having an internal wall surface and connected
      to said dialysate supply unit, and
      a dialysate A stock solution tank connected to said dialysate supply unit;
   a unit for preparing electrolyzed hyperacidity water;
   a tank for holding the electrolyzed hyperacidity water connected to said unit for preparing electrolyzed hyperacidity water;
   a shower arranged inside and at the top of said dialysate B stock solution tank, said shower having nozzle orifices directed toward the internal wall surface of said dialysis B stock solution tank; and
   an electrolyzed hyperacidity water supply line for transporting said electrolyzed hyperacidity water, which supply line extends from said tank for holding the electrolyzed hyperacidity water to said shower.

2. The apparatus according to claim 1, further comprising a second electrolyzed hyperacidity water supply line for transporting the electrolyzed hyperacidity water, which said second supply line extends from said tank for holding the electrolyzed hyperacidity water to said dialysate supply unit.

3. The apparatus according to claim 1, further comprising a third an electrolyzed hyperacidity water supply line for transporting the electrolyzed hyperacidity water, which said third supply line extends from said tank for holding the electrolyzed hyperacidity water to said tank for holding pure water.

4. An apparatus for cleaning and disinfecting hemodialysis equipment as claimed in claim 1, wherein the electrolyzed hyperacidity water has a pH value of about 2.7–2.3, a redox potential of about 1000 to 1200 mv and an effective chlorine concentration of 10–40 ppm.

5. An apparatus for cleaning and disinfecting hemodialysis equipment, wherein the apparatus comprises:
   hemodialysis equipment comprising
      a dialysate supply unit,
      a tank for holding pure water,
      a dialysate B stock solution tank having an internal wall surface and connected to said dialysate supply unit,
      a dialysate A stock solution tank connected to said dialysate supply unit, and
      a pure water supply line extending from said tank for holding pure water to said dialysate supply unit;
   a unit for preparing electrolyzed hyperacidity water;
   a tank for holding said electrolyzed hyperacidity water connected to said unit for preparing electrolyzed hyperacidity water;
   a shower arranged inside and at the top of said dialysate B stock solution tank, said shower having nozzle orifices directed toward the internal wall surface of said dialysate B stock solution tank; and
   an electrolyzed hyperacidity water supply line for transporting said electrolyzed hyperacidity water which extends from said tank for holding said electrolyzed hyperacidity water to said shower or to said shower and said dialysate supply unit; and
   a solenoid valve being disposed in the electrolyzed hyperacidity water supply line.

6. The apparatus according to claim 5, wherein said electrolyzed hyperacidity water supply line extends to said dialysate B stock solution tank and said electrolyzed hyperacidity water supply line comprises:
   (iv-1) a line which is connected from said tank for holding the electrolyzed hyperacidity water to said pure water supply line;
   (iv-2) a line branching out from said pure water supply line downstream of the connection point between said line (iv-1) and said pure water supply line, said line (iv-2) extending to said dialysate B stock solution tank; and
   (iv-3) the part of said pure water supply line which extends from the connection point between said pure water supply line and said line (iv-1) to the connection point between said branching line (iv-2) and said pure water supply line; and
   a solenoid valve disposed in said line (iv-1), a solenoid valve disposed in said branching line (iv-2), and a solenoid valve disposed upstream of the connection point between said pure water supply line and the line (iv-1).

7. The apparatus according to claim 6, further comprising a second electrolyzed hyperacidity water supply line which extends from said tank for holding the electrolyzed hyperacidity water to the tank for holding pure water said second electrolyzed hyperacidity water supply line having a valve for closing or opening said supply line.

8. The apparatus according to claim 5, wherein said electrolyzed hyperacidity water supply line extends to said dialysate supply unit and said electrolyzed hyperacidity water supply line comprises:
   (iv-1) a line which is connected from said tank for holding the electrolyzed hyperacidity water to said pure water supply line;
   (iv-4) a line which extends from a connection point between the line (iv-1) and the pure water supply line to said dialysate supply unit; and a solenoid valve disposed in said line (iv-1), and a solenoid valve disposed upstream of the connection point between said pure water supply line and the line (iv-1).

9. The apparatus according to claim 8, further comprising a second electrolyzed hyperacidity water supply line which extends from said tank for holding the electrolyzed hyperacidity water to the tank for holding pure water, the second electrolyzed hyperacidity water supply line having a valve for closing or opening said supply line.

10. An apparatus for cleaning and disinfecting hemodialysis equipment as claimed in claim 5, wherein the electrolyzed hyperacidity water has a pH value of about 2.7–2.3, a redox potential of about 1000 to 1200 mv and an effective chlorine concentration of 10–40 ppm.

11. An apparatus for cleaning and disinfecting hemodialysis equipment comprising:

a unit for preparing electrolyzed hyperacidity water;

a tank for holding said electrolyzed hyperacidity water connected to said unit for preparing electrolyzed hyperacidity water;

a dialysate B stock solution tank having an internal wall surface;

a shower arranged inside and at the top of said dialysate B stock solution tank, said shower having nozzle orifices directed toward the internal wall surface of said dialysate B stock solution tank; and an electrolyzed hyperacidity water supply line for transporting said electrolyzed hyperacidity water which extends from said tank for holding the electrolyzed hyperacidity water to said shower.

12. The apparatus according to claim 11, further comprising a second electrolyzed hyperacidity water supply line which extends from said tank for holding the electrolyzed hyperacidity water to the hemodialysis equipment and a solenoid valve disposed in said line second electrolyzed hyperacidity water supply line.

13. The apparatus according to claim 12, further comprising a third electrolyzed hyperacidity water supply line which extends from said tank for holding the electrolyzed hyperacidity water to the hemodialysis equipment.

14. An apparatus for cleaning and disinfecting hemodialysis equipment as claimed in claim 11, wherein the electrolyzed hyperacidity water has a pH value of about 2.7–2.3, a redox potential of about 1000 to 1200 mv and an effective chlorine concentration of 10–40 ppm.

* * * * *

UNITED STATES PATENT AND TRADEMARK OFFICE
CERTIFICATE OF CORRECTION

PATENT NO. : 6,022,512
DATED : February 8, 2000
INVENTOR(S) : Noriaki TANAKA, Tomiya ABE It is certified that error appears in the above-indentified patent and that said Letters Patent is hereby corrected as shown below:

On the title page, item

[75] Inventors: Noriaki Tanaka, 707, Kitanoda, Sakai-shi, Osaka-fu; Tomiya Abe, [Wakayma] 790-31, Nishinosho, Wakayama-shi, Wakayama-ken, both of Japan Signed and Sealed this Twenty-seventh Day of March, 2001

*Attest:*

NICHOLAS P. GODICI

*Attesting Officer*   *Acting Director of the United States Patent and Trademark Office*